(12) United States Patent
Guo et al.

(10) Patent No.: US 11,980,849 B2
(45) Date of Patent: May 14, 2024

(54) BACTERIOPHAGE-DERIVED NANOPORE SENSORS

(71) Applicants: Ohio State Innovation Foundation, Columbus, OH (US); Oxford Nanopore Technologies Limited, Oxford Oxfordshire (GB)

(72) Inventors: Peixuan Guo, Dublin, OH (US); Zhouxiang Ji, Columbus, OH (US); Lakmal Jayasinghe, Headington (GB); Michael Jordan, Oxford Oxfordshire (GB)

(73) Assignee: Ohio State Innovation Foundation, Columbus, OH (US)

( * ) Notice: Subject to any disclaimer, the term of this patent is extended or adjusted under 35 U.S.C. 154(b) by 877 days.

(21) Appl. No.: 16/967,560

(22) PCT Filed: Feb. 8, 2019

(86) PCT No.: PCT/US2019/017329
§ 371 (c)(1),
(2) Date: Aug. 5, 2020

(87) PCT Pub. No.: WO2019/157365
PCT Pub. Date: Aug. 15, 2019

(65) Prior Publication Data
US 2021/0086141 A1    Mar. 25, 2021

Related U.S. Application Data

(60) Provisional application No. 62/628,562, filed on Feb. 9, 2018.

(51) Int. Cl.
B01D 69/14    (2006.01)
B01D 67/00    (2006.01)
(Continued)

(52) U.S. Cl.
CPC ....... B01D 69/144 (2013.01); B01D 67/0081 (2013.01); B01D 71/74 (2013.01);
(Continued)

(58) Field of Classification Search
None
See application file for complete search history.

(56) References Cited

U.S. PATENT DOCUMENTS

2014/0262784 A1* 9/2014 Clarke ................. C12Q 1/6869
204/603
2015/0191709 A1* 7/2015 Heron ................. C12Q 1/6827
435/375
(Continued)

FOREIGN PATENT DOCUMENTS

WO    2010062697 A2    6/2010
WO    2016059375 A1    4/2016
(Continued)

OTHER PUBLICATIONS

International Search Report issued for PCT/US2019/017329, mailed Jun. 28, 2019.
(Continued)

Primary Examiner — J. Christopher Ball
(74) Attorney, Agent, or Firm — Thomas | Horstemeyer, LLP

(57) ABSTRACT

Disclosed herein are compositions and methods that involve inserting connector protein channels of bacteriophage DNA packaging motors into copolymeric membranes via liposome-polymer fusion, which can be used as nanopore sensors for biomedical applications such as high throughput protein sequencing or cancer diagnosis. For example, disclosed are compositions comprising a copolymeric membrane into which a connector protein channel of a bacteriophage packaging motor has been inserted.

16 Claims, 18 Drawing Sheets

(51) Int. Cl.
  *B01D 71/74* (2006.01)
  *B01D 71/80* (2006.01)
  *C12Q 1/6869* (2018.01)
(52) U.S. Cl.
  CPC ........... *B01D 71/80* (2013.01); *C12Q 1/6869* (2013.01); *C12Q 2535/122* (2013.01); *C12Q 2563/116* (2013.01); *C12Q 2565/607* (2013.01); *C12Q 2565/631* (2013.01)

(56) References Cited

U.S. PATENT DOCUMENTS

2015/0267253 A1  9/2015 Guo
2017/0058337 A1  3/2017 Clarke et al.
2017/0058338 A1  3/2017 Jayasinghe et al.
2017/0253910 A1  9/2017 Brown et al.

FOREIGN PATENT DOCUMENTS

WO  2017004463     1/2017
WO  2017049101 A2  3/2017

OTHER PUBLICATIONS

Chinese Office Action and Search Report, CN Patent Application No. 201980012258.4, issued May 12, 2023.
Supplementary European Search Report issued for EP19751833, mailed Oct. 7, 2021.
Agirrezabala et al., Maturation of phage T7 involves structural modification of both shell and inner core components, The EMBO Journal, 24, 3820-3829, 2005.
Altschul et al., Gapped BLAST and PSI-BLAST: a new generation of protein database search programs, Nucleic Acids Research, vol. 25, No. 17 3389-3402, 1997.
Carazo et al., Bacteriophage T3 Gene 8 Product Oligomer Structure, Journal of Ultrastructure and Molecular Structure Research, 94, 105-113, 1986.
Cerritelli et al., Purification and Characterization of T7 Head-Tail Connectors Expressed from the Cloned Gene, J. Mol. Biol., 258, 299-307, 1996.
Cingolani et al., Preliminary crystallographic analysis of the bacteriophage P22 portal protein, Journal of Structural Biology 139, 46-54, 2002.
Colas et al., Microscopical investigations of nisin-loaded nanoliposomes prepared by Mozafari method and their bacterial targeting, Micron 38, 841-847, 2007.
Driedonks et al., Gene 20 Product of Bacteriophage T4 Its Purification and Structure, J. Mol. Biol., 152, 641-662, 1981.
Geng et al., Three reversible and controllable discrete steps of channel gating of a viral DNA packaging motor, Biomaterials, 32(32): 8234-8242, 2011.
Gonzalez-Perez et al., Biomimetic Triblock Copolymer Membrane Arrays: A Stable Template for Functional Membrane Proteins, Langmuir, 25(18), 10447-10450, 2009.

Guasch et al., Purifcation, crystallization and preliminary X-ray diffraction studies of the bacteriophage Φ29 connector particle, FEBS Letters 430, 283-287, 1998.
Guo et al., Construction and 3-D Computer Modeling of Connector Arrays with Tetragonal to Decagonal Transition Induced by pRNA of phi29 DNA-Packaging Motor, Journal of Nanoscience and Nanotechnology vol. 5, 856-863, 2005.
Haque et al., Real-Time Sensing and Discrimination of Single Chemicals Using the Channel of Phi29 DNA Packaging Nanomotor, ACS Nano Vol. 6, No. 4, p. 3251-3261, 2012.
Haque et al., Incorporation of viral DNA packaging motor channel in lipid bilayers for real-time, single-molecule sensing of chemicals and double-stranded DNA, Nat Protoc., 8(2), 1-38, 2013.
Heron et al., Simultaneous Measurement of Ionic Current and Fluorescence from Single Protein Pores, J. Am. Chem. Soc., 131 (5), 1652-1653, 2009.
Ibanez et al., Overproduction and purification of the connector protein of Bacillus subtiis phage Φ29, vol. 12, No. 5, Nucleic Acids Research , 2351-2365, 1984.
Ivanov et al., DNA Tunneling Detector Embedded in a Nanopore, Nano Lett., 11, 279-285, 2011.
Kochan et al., Bacteriophage Lambda Preconnectors Purification and Structure, J. Mol. Biol., 174, 433-447, 1984.
Lieberman et al., Processive Replication of Single DNA Molecules in a Nanopore Catalyzed by phi29 DNA Polymerase, J Am Chem Soc., 132(50): 17961-17972, 2010.
Morais et al., Defining Molecular and Domain Boundaries in the Bacteriophage φ29 DNA Packaging Motor, Structure, 16(8): 1267-1274, 2008.
Nutter et al., Change in Methylation of Salmonella Bacteriophage P3 Deoxyribonucleic Acid with Host-Controlled Modification by *Escherichia coli*1, Journal of Virology, p. 560-562, 1972.
Robinson et al., Affinity of molecular interactions in the bacteriophage φ29 DNA packaging motor, Nucleic Acids Research, vol. 34, No. 9, 2698-2709, 2006.
Soni et al., Synchronous optical and electrical detection of biomolecules traversing through solid-state nanopores, Review of Scientific Instruments 81, 014301, 2010.
Staley, Measurement of in Situ Activities of Nonphotosynthetic Microorganisms in Aquatic and Terrestrial Habitats, Ann. Rev. Microbiol., 39:321-46, 1985.
Stoddart et al., Single-nucleotide discrimination in immobilized DNA oligonucleotides with a biological nanopore, PNAS vol. 106, No. 19, 7702-7707, 2009.
Wang et al., Three-step Channel Conformational Changes Common to DNA Packaging Motors of Bacterial Viruses T3, T4, SPP1, and Phi29, Virology, 500: 285-291, 2017.
Wendell et al., Translocation of double-stranded DNA through membrane-adapted phi29 motor protein nanopores, Nature Nanotechnology, vol. 4, 765-772, 2009.
Wendell et al., Translocation of double stranded DNA through membrane adapted phi29 motor protein nanopore, Nat Nanotechnol., 4(11): 765-772, 2009.
Xiao et al., Fabrication of Massive Sheets of Single Layer Patterned Arrays Using Lipid Directed Reengineered Phi29 Motor Dodecamer, ACS Nano, vol. 3, No. 1, p. 100-107, 2009.

* cited by examiner

BACTERIOPHAGE-DERIVED NANOPORE SENSORS

CROSS-REFERENCE TO RELATED APPLICATIONS

This application is a National Stage of International Application No. PCT/US2019/017329, filed Feb. 8, 2019, which claims benefit of U.S. Provisional Application No. 62/628,562, filed Feb. 9, 2018, which is hereby incorporated herein by reference in its entirety.

STATEMENT REGARDING FEDERALLY SPONSORED RESEARCH OR DEVELOPMENT

This invention was made with Government Support under Grant No. EB012135 awarded by the National Institutes of Health. The Government has certain rights in the invention.

BACKGROUND

A wide range of protein antigens have been proved useful as cancer biomarkers for early detection, diagnosis or prediction, such as cancer antigen 125, human epididymis protein 4, PSA, prostate-specific membrane antigen (PSMA), etc. Traditional biochemical assays such as ELISA, Western Blot, mass spectrometry, and fluorescence imaging have been used in the diagnosis of cancer. However, these classic approaches have limited applicability in an industrial setting due to their time-consuming and labor-intensive sample preparation, low sensitivity, or low accuracy.

The advancement of nanopore technology has inspired a range of biomedical applications, such as nucleic acids, chemicals, peptide or protein sensing. Nanopore-based sensing at single-molecule level promises to overcome some of the drawbacks of traditional approaches. Nanopores of both biological and synthetic origin are used for specifically identifying analytes using tunable resistive pulse sensing, whereby analytes of interest are driven through a pore with nanometer size by electric force and identified by ionic signature profiles. In contrast to synthetic nanopores, biological nanopores are homogenous and easy to obtain and purify at large-scale. Availability of crystal structure information allows precise modification of biological nanopores for specific sensing applications. The nanopores are based on naturally occurring membrane proteins and can be inserted into a copolymer membrane by contacting the membrane with the purified protein and applying a voltage potential to the membrane.

The bacteriophage phi29 nanochannel, which is not a natural membrane protein, has been developed into a powerful nanopore-based platform for the fingerprinting of chemicals, DNAs, RNAs, peptides and antibodies at single-molecule level. The nanochannel is inserted into liposomes and fused with planar lipid bilayers. Analytes are driven through the phi29 nanochannel by electric force, thus temporarily blocking the flow of ions and causing an electronic blockage signal. Furthermore, analytes that bind to ligands attached or genetically engineered into the phi29 nanochannel result in conformational changes in the channel that are observed in electronic signal profiles. However, a high throughput approach is desirable in order to achieve protein sequencing or multiple biomarker detection in a test panel.

SUMMARY

Disclosed herein are methods for inserting connector protein channels of bacteriophage DNA packaging motors into copolymeric membranes for use as nanopores. The bacteriophage phi29 nanochannel is not a natural membrane protein and the purified protein cannot be inserted into a copolymer membrane. Insertion is achieved by fusing a liposome into which the connector protein channel is inserted with a copolymer membrane. The membrane so produced is a copolymer membrane comprising the connector protein channel. The copolymer membrane may also comprise lipids from the liposome fused with the copolymer membrane.

Therefore, also disclosed are compositions comprising a copolymeric membrane into which a connector protein channel of a bacteriophage packaging motor has been inserted. The compositions can be used as nanopore sensors for biomedical applications such as high throughput protein sequencing or cancer diagnosis.

Embedding the connector protein channels into copolymeric membranes allows them to be used as nanopores in high throughput instruments. For example, Oxford Nanopore Technologies Ltd. (ONT) has developed an electronics-based high throughput nanopore sensing technology to analyze various types of analytes. Users can choose different types of ONT instruments (eg: SmidgION, MinION, GridION, PromethION) for different experiments and they can be fitted with different types of flow cells in which the nanopore is embedded in a copolymeric membrane. The ONT polymeric membrane is stable at least for a few months and also resistant to higher voltages. This use of nanopores allows for high-throughput, simultaneous detection of many types of cancer biomarkers and enables applications such as protein sequencing. Each channel can contain its own pair of electrodes, thus separating electrical signals between channels. Disclosed herein is a method of inserting portal proteins of bacteriophage phi29 into a copolymeric membrane. In one embodiment, the membrane may be present in a device suitable for high throughput sequencing.

In particular, Oxford Nanopore Technologies Ltd. has developed the MinION device with a multiplexed chip with 512 channels. Such high-throughput detection allows the simultaneous detection of many types of cancer biomarkers and enables applications such as protein sequencing. Each channel contains its own pair of electrodes, thus separating electrical signals between channels. Further, MinION uses triblock copolymer membranes, which are more stable than traditional lipid membranes. Disclosed herein is a method of inserting portal proteins of bacteriophage phi29 into the MinION device for biomedical applications such as high throughput protein sequencing or cancer diagnosis.

In some embodiments, the method of inserting portal proteins of bacteriophage phi29 into a copolymeric membrane involves incorporating connector protein channels of bacteriophage DNA packaging motors into liposomes, contacting a copolymeric membrane with the liposomes, and inducing liposome-polymer fusion by application of voltage across the copolymer membrane. Hence a method of inserting a nanopore derived from a connector protein of a bacteriophage DNA packaging motor into a copolymeric membrane, the method comprising contacting the copolymeric membrane with a liposome comprising the nanopore, and applying a voltage across the copolymeric membrane to induce liposome-copolymer fusion is disclosed. The nanopore derived from a connector protein of a bacteriophage DNA packaging motor, may be any of the nanopores defined herein.

Examples of bacteriophage DNA packaging motors that contain connector protein channels suitable for use in the disclosed compositions and methods include, but are not limited to), phi29 (Accession No. YP_002004539.1), T3 (Accession No. NP_523332.1), T4 (Accession No. NP_049782.1), T5 (Accession No. AAS77191.1), T7 (Accession No. NP_041995.1), SPP1 (Accession No. CAA66580.1), HK97 (Accession No. NP_037699.1), G20c (Accession No. KX987127.1), phage 2 (Acc. No. NP_046757), phage 3 (Nutter et al., 1972 J. Viral. 10(3): 560-2), phage 22 (Acc. No. AAA72961) and lambda phage (Acc. Nos. gi 549295, gi 6723246, gi 15837315, gi 16764273) DNA packaging motors. In some embodiments, the connector protein comprises bacteriophage phi29 connector protein gp10. In some embodiments, the connector protein comprises bacteriophage T3 connector protein gp8. In some embodiments, the connector protein comprises bacteriophage T7 connector protein gp8. In some embodiments, the connector protein comprises bacteriophage T4 connector protein gp20. In some embodiments, the connector protein comprises bacteriophage T5 connector protein gp7. In some embodiments, the connector protein comprises bacteriophage SPP1 connector protein gp6. In some embodiments, the connector protein comprises bacteriophage HK97 connector protein gp3.

Therefore, disclosed herein is a nanopore sensor that comprises a connector protein channel of bacteriophage DNA packaging motor incorporated into a copolymeric membrane. In particular, disclosed herein is a copolymeric membrane comprising a nanopore, wherein the nanopore is derived from a connector protein of a bacteriophage DNA packaging motor.

In some embodiments, the copolymer membrane is a triblock or diblock copolymer membrane. By virtue of how the nanopore is inserted into the copolymer membrane, the copolymer membrane comprising the nanopore may, in some embodiments, further comprise one or more lipids. In some embodiments, the copolymeric membrane is an amphiphilic ABA type tri-block copolymer membrane. For example, the membrane can be formed by contacting a polar medium with an apolar medium containing ABA molecules, which results in spontaneous formation of a layer of the ABA molecules around the polar medium, at the apolar-polar interface. When two such volumes of polar media are then brought together, through the apolar medium, a stable membrane of ABA molecules forms at the interface between the first and second polar volumes. The resultant membrane, being synthetic, has been shown to be robust, stable and less susceptible to degradation from detergents and proteins than conventional lipid systems. The membrane is also able to withstand larger potential differences applied across it.

Additionally disclosed herein is an array of copolymeric membranes comprising nanopores derived from a connector protein of a bacteriophage DNA packaging motor. In one embodiment, the array is adapted for insertion into a device suitable for detecting the translocation of analytes through the nanopores in the array. An array of nanopores may be provided to increase the throughput and therefore the measurement of polynucleotide strands, such as a disclosed in International Application WO2014/064443, which is hereby incorporated herein by reference in its entirety.

Also disclosed is a device comprising an array of copolymeric membranes in which nanopores derived from a connector protein of a bacteriophage DNA packaging motor are inserted, a means for applying a voltage potential across the membranes and a means for detecting electrical changes across the membranes. In one embodiment, the device further comprises a fluidics system configured to controllably supply a sample to be characterized to the membranes.

Further disclosed is a method of characterizing a target analyte, the method comprising contacting the copolymeric membrane comprising a nanopore derived from a connector protein of a bacteriophage DNA packaging motor with the target analyte such that the target analyte moves with respect to the nanopore, and taking one or more measurements as the target analyte moves with respect to the pore, thereby determining the presence, absence or one or more characteristics of the analyte. In some embodiments, the measurements are electrical measurements and/or optical measurements. In some embodiments, the target analyte is associated with a medical condition.

In some embodiments of various aspects described herein, the method may further comprise, upon application of a potential across the membrane, detecting a signal in response to an analyte (e.g., the by-products of the processing of a polynucleotide by a polymerase) passing through the nanopore. In some embodiments, a potential difference can be driven by osmotic imbalance providing ion flow. In some embodiments, a potential difference may be applied across the nanopore between two electrodes positioned on either side the nanopore. The signal may be an electrical measurement and/or an optical measurement. Possible electrical measurements include: current measurements, impedance measurements, tunneling or electron tunneling measurements (Ivanov A P et al., Nano Lett. 2011 Jan. 12; 11(1):279-85), and FET measurements (International Application WO 2005/124888), e.g., voltage FET measurements. Optical measurements may be combined with electrical measurements (Soni G V et al., Rev Sci Instrum. 2010 January; 81(1):014301). The measurement may be a transmembrane current measurement such as measurement of ionic current flowing through the nanopore.

Alternatively the measurement may be a fluorescence measurement indicative of ion flow through the channel such as disclosed by Heron et al, J. Am. Chem. Soc., 2009, 131 (5), 1652-1653 or measurement of a voltage across the membrane using a FET. In some embodiments, the method may further comprise, upon application of a potential across the membrane, detecting an ionic current flow through the nanopore as a polynucleotide is processed. In some embodiments, the methods may be carried out using a patch clamp or a voltage clamp. In some embodiments, the methods may be carried out using a voltage clamp. Electrical measurements may be made using standard single channel recording equipment as describe in Stoddart D et al., Proc Natl Acad Sci, 12; 106(19):7702-7, Lieberman K R et al, J Am Chem Soc. 2010; 132(50):17961-72, and International Application WO 2000/28312. Alternatively, electrical measurements may be made using a multi-channel system, for example as described in International Application WO 2009/077734 and International Application WO 2011/067559, which are hereby incorporated herein by reference in entirety.

Also disclosed herein is a method of characterizing a target analyte that involves applying an electrical potential across a nanopore sensor disclosed herein, contacting the nanopore sensor with the target analyte such that the target analyte passes through the nanopore, and detecting an effect of the target analyte on electrical conductivity through the nanopore sensor.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 3A shows control of Channel 86 of MinION before connector insertion. FIG. 3B shows three-step gating of single phi29 connector induced by 100 mV for Channel 86.

FIG. 4A shows control of Channel 304 before channel insertion. FIG. 4B shows peptide was translocated through single phi29 connector which was located at Channel 304.

FIG. 5A shows current trace of single channel of phi29 under the voltage of 50 mV. FIG. 5B shows single phi29 channel insertion into the lipid bilayer membrane measured by electrophysiology assay with MinION flow cell buffer under the voltage of ±50 mV. FIG. 5C shows three-step gating of single phi29 channel under the voltage of 100 mV. Line indicates applied voltage.

DETAILED DESCRIPTION

Figure 1:
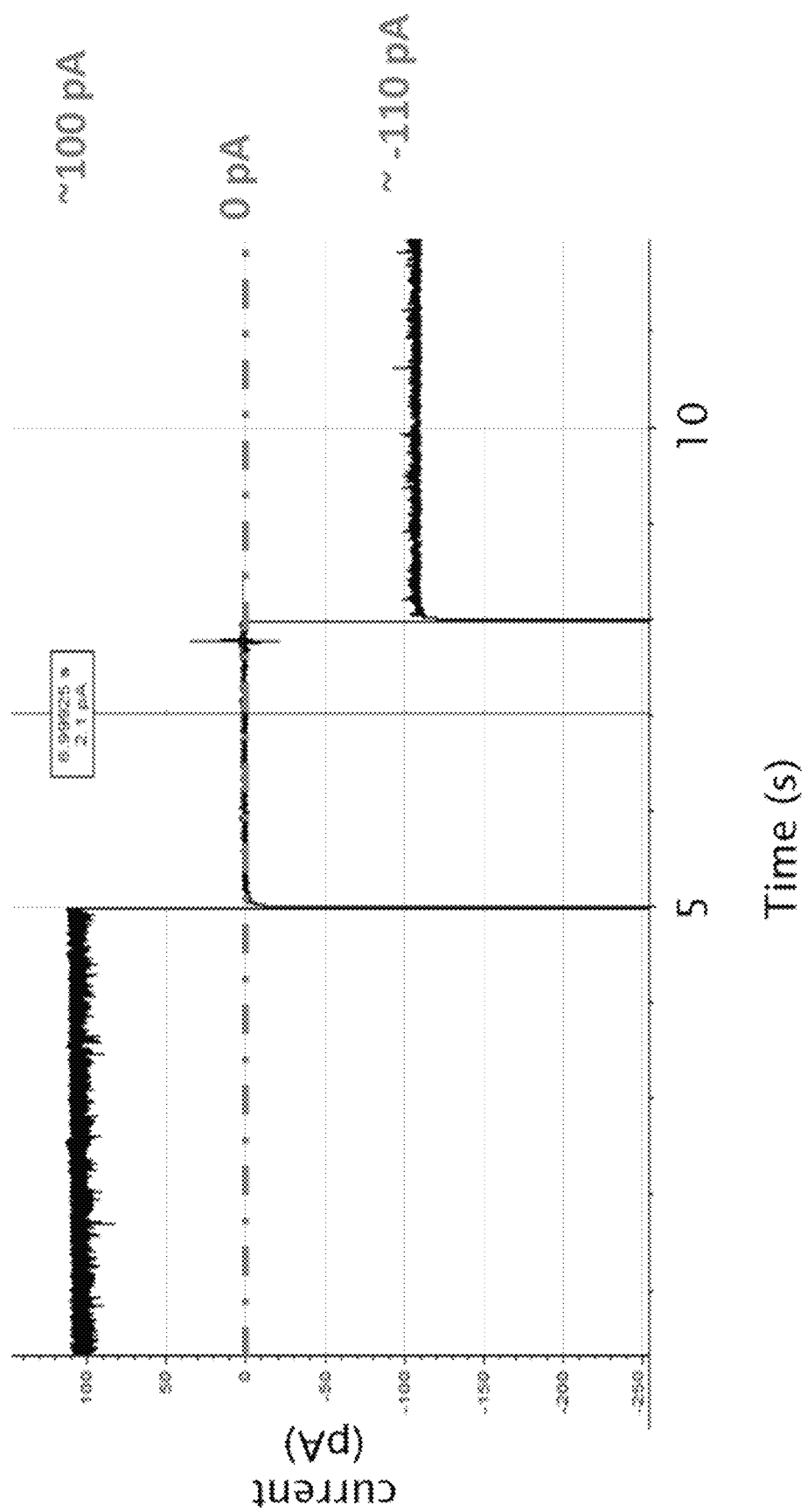
FIG. 1 shows single channel of C-his gp10/liposome insertion into lipid membrane using MinION conductance buffer. Applied voltage: +50 mV or −50 mV.
Figure 2A:
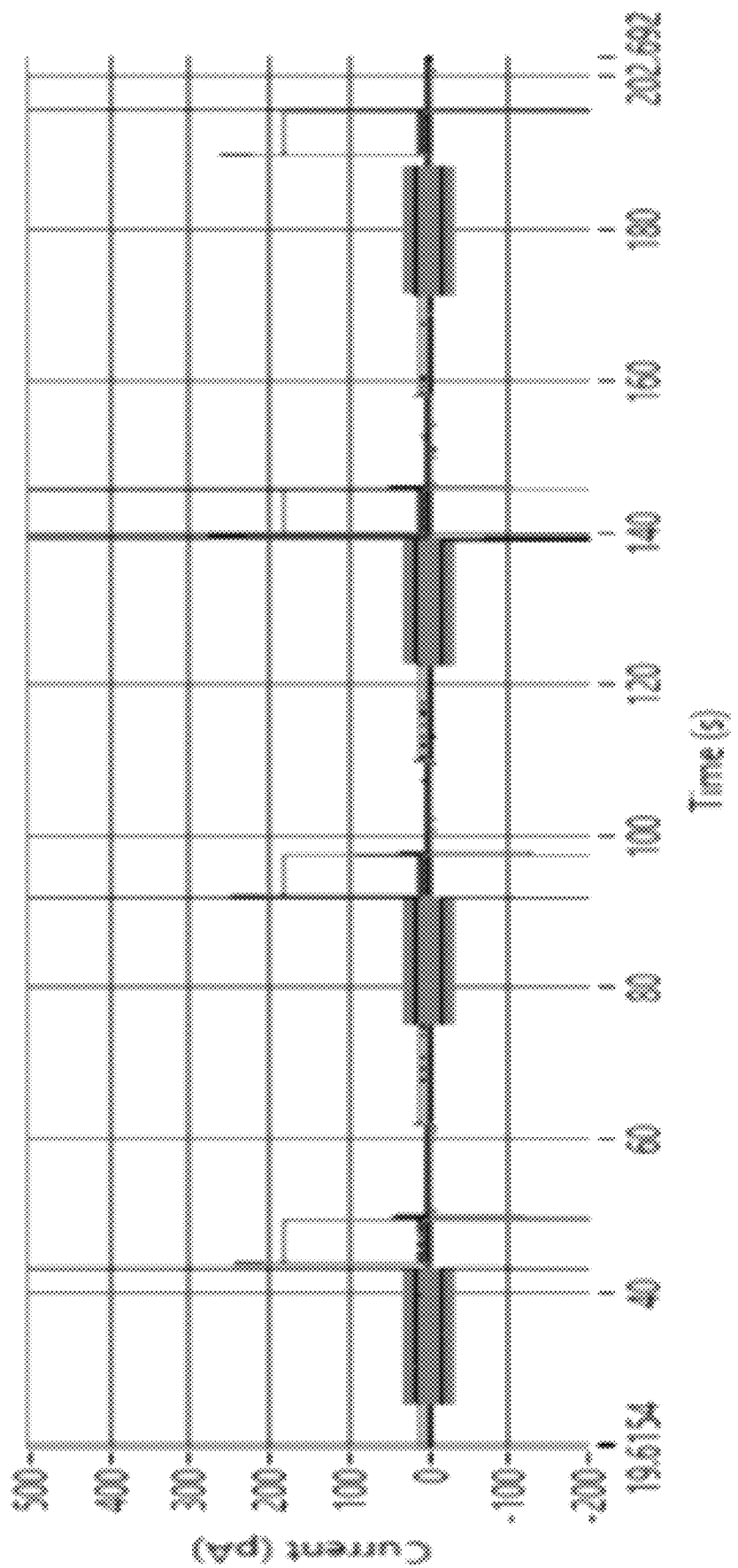
FIGS. 2A to 2D shows single phi29 channel insertion on the Channel 256 and 267 of MinION. The currents of Channel 256 (FIG. 2A) and 267 (FIG. 2B) before connector insertion were around 0 pA. Single channel insertion was from Channel 256 (FIG. 2C, applied voltage; 100 mV) and 267 (FIG. 2D, applied voltage: 180 mV) under different voltages.
Figure 2B:
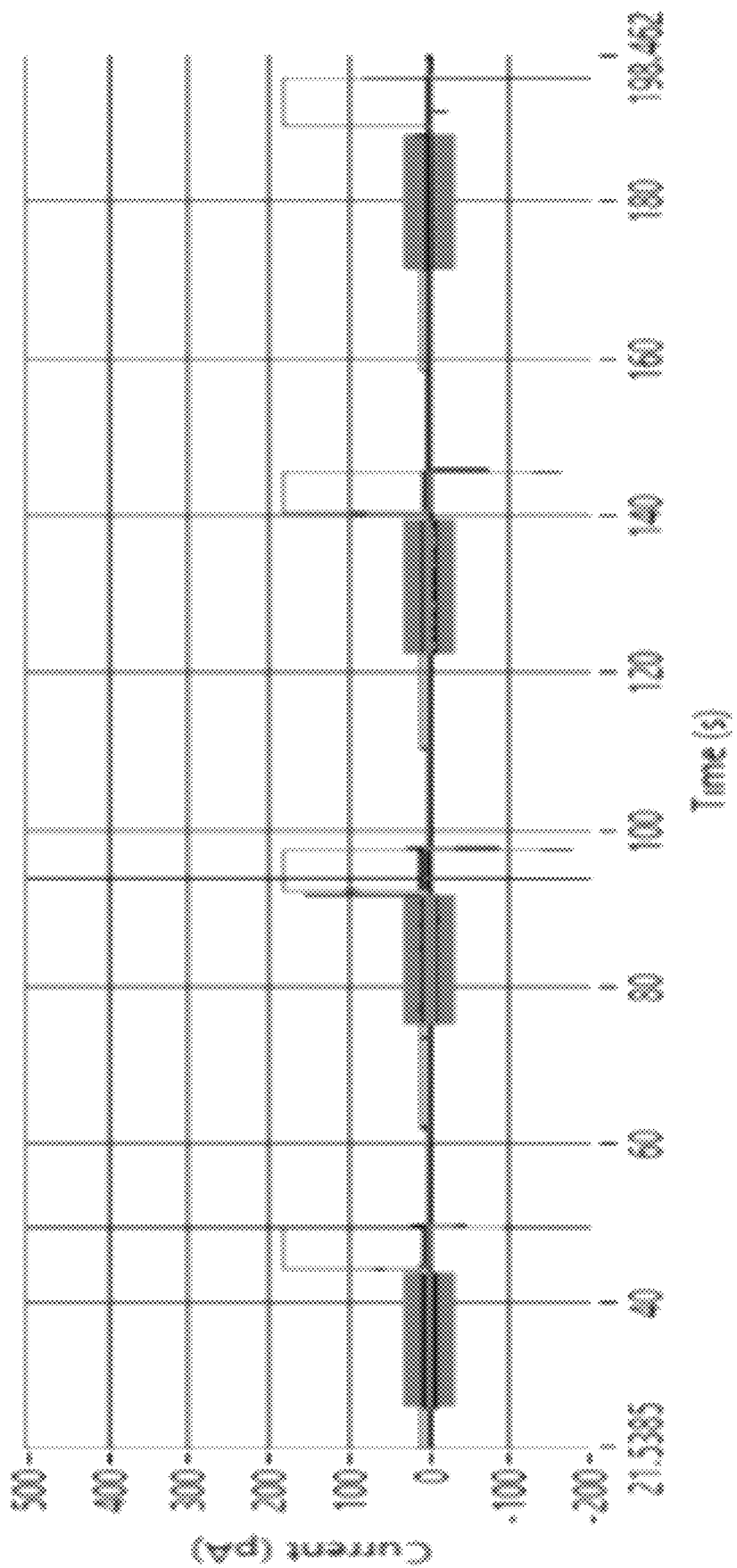
Figure 2C:
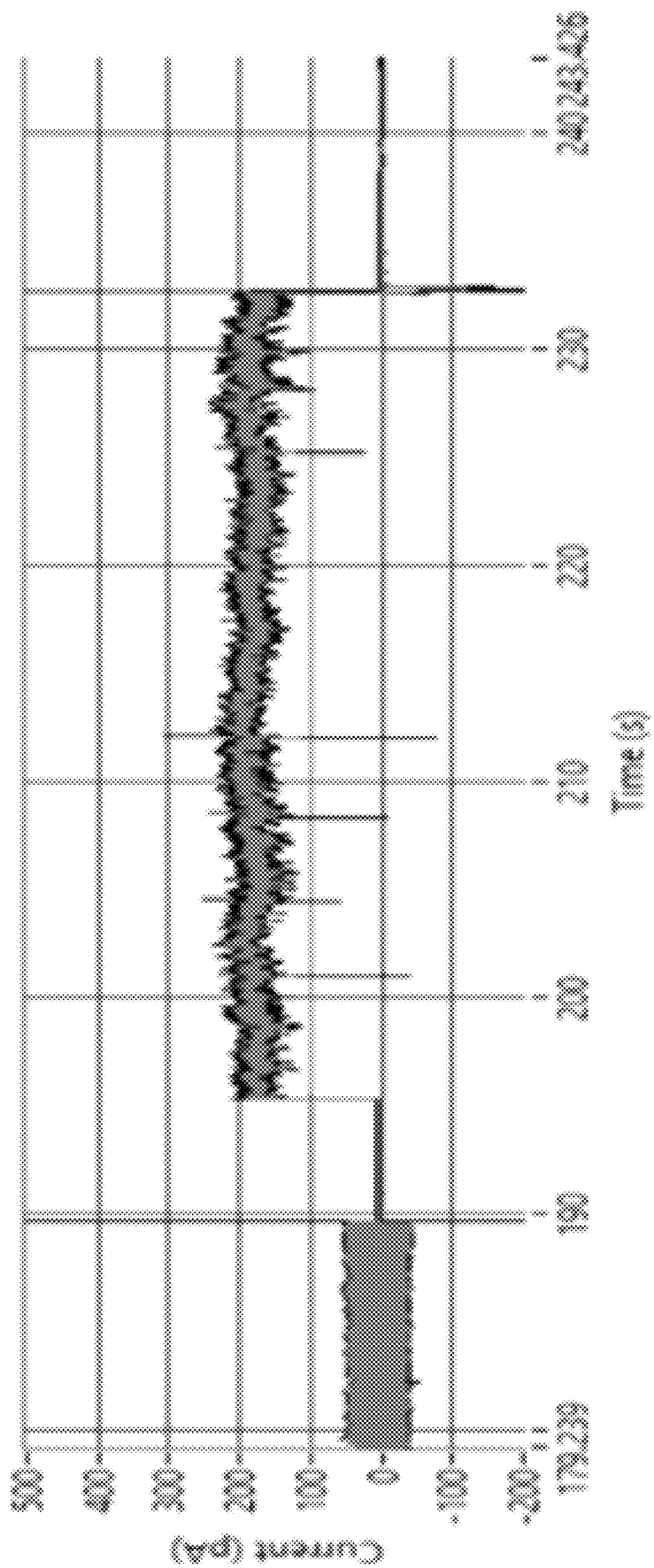
Figure 2D:
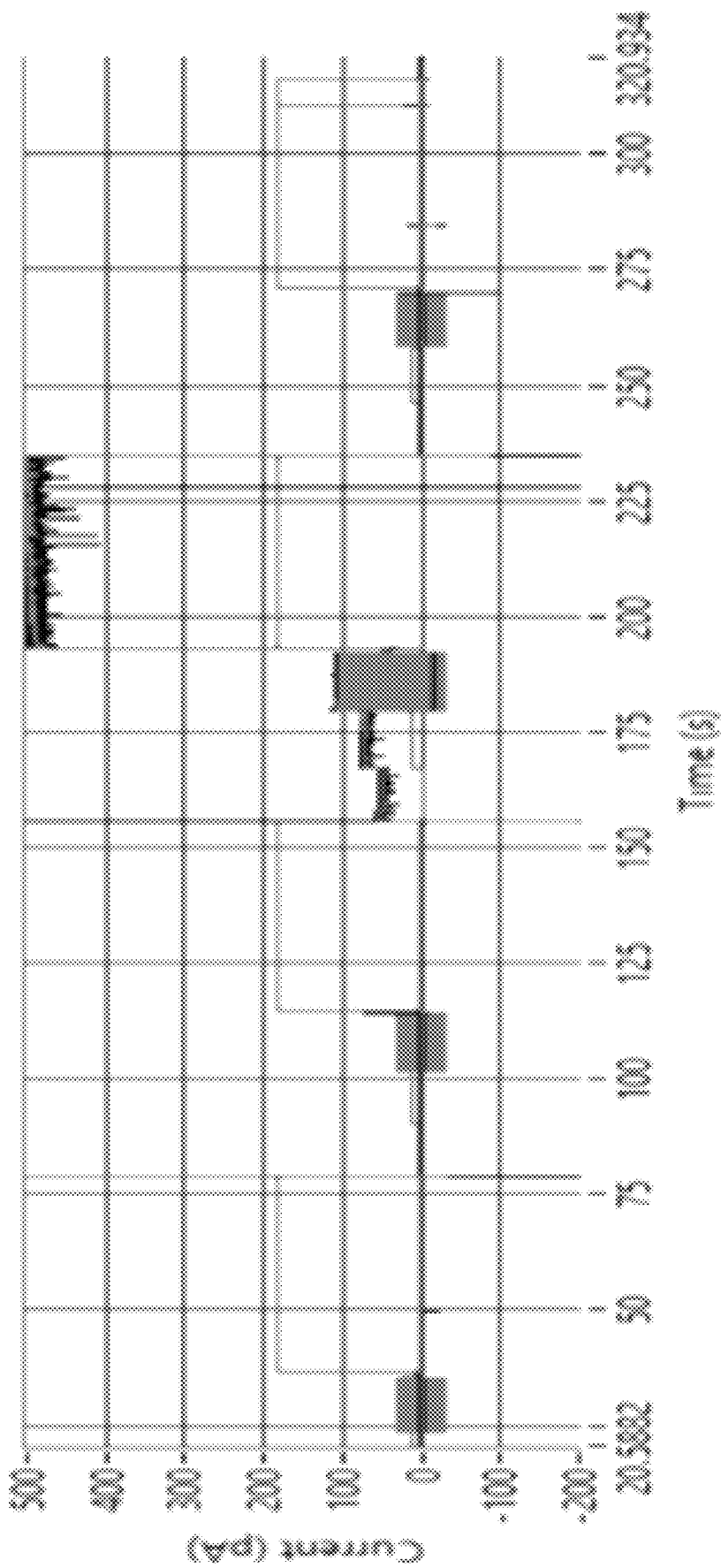
Figure 3A:
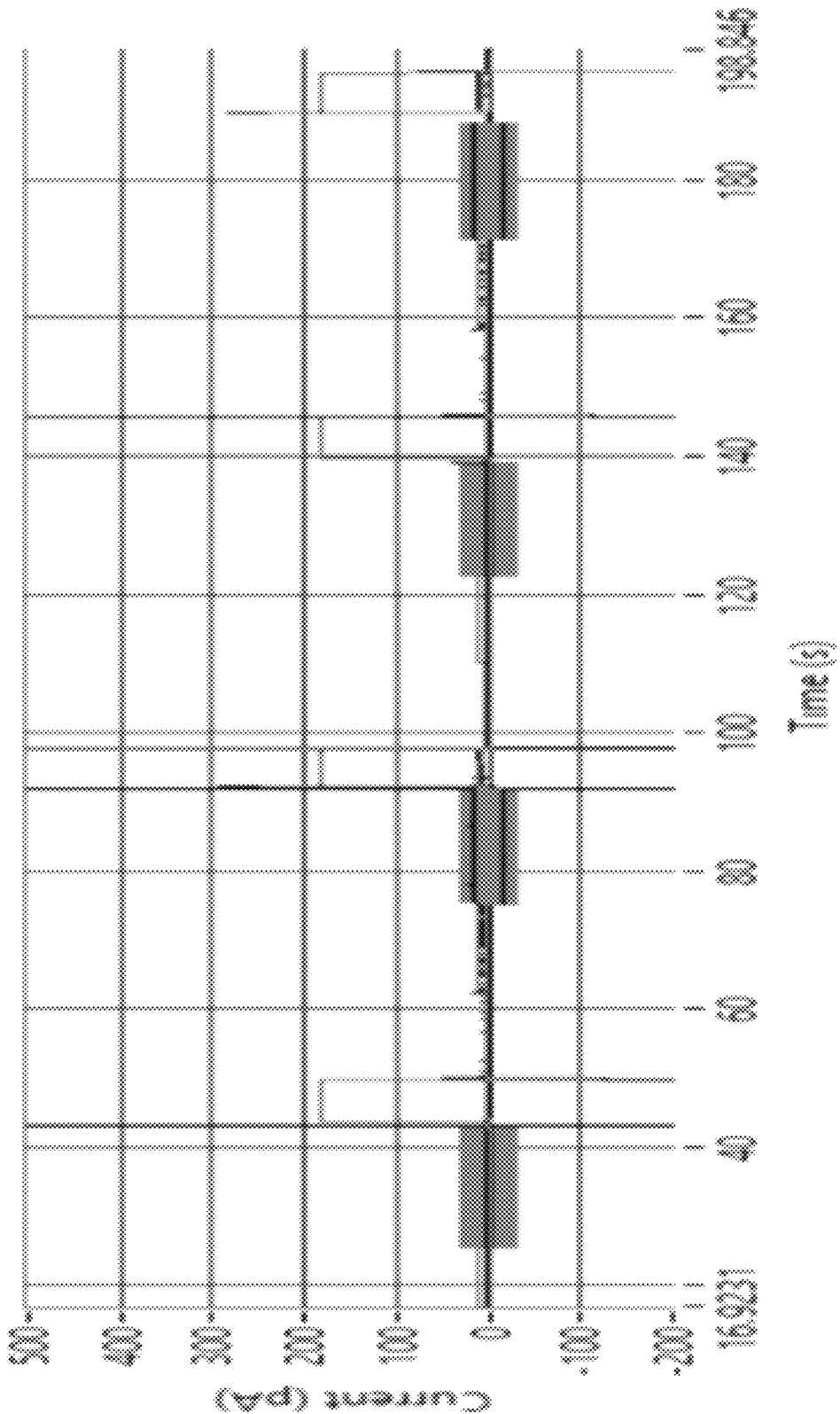
FIGS. 3A and 3B show three-step gating of single phi29 connector to confirm channel insertion.
Figure 3B:
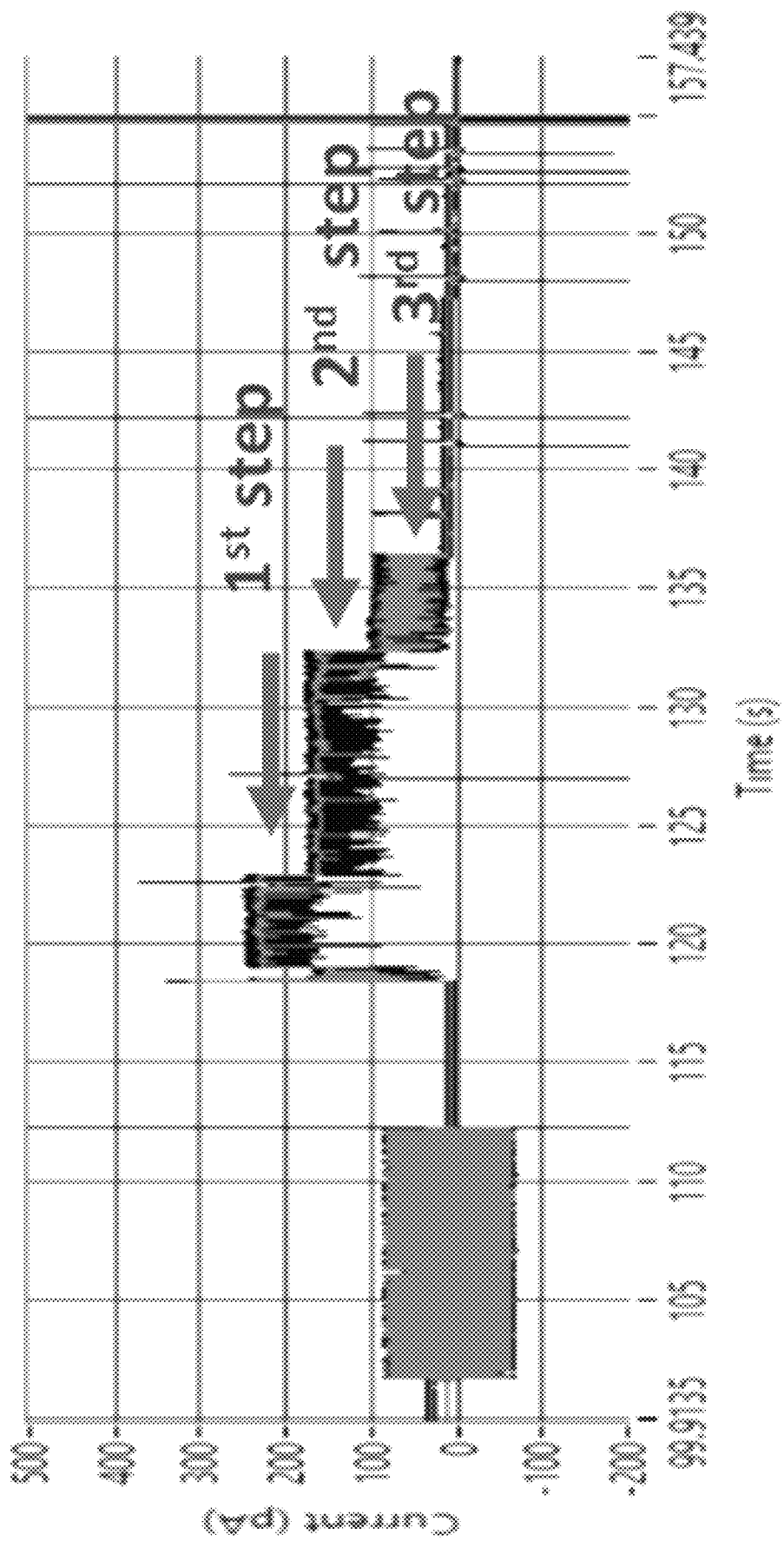
Figure 4A:
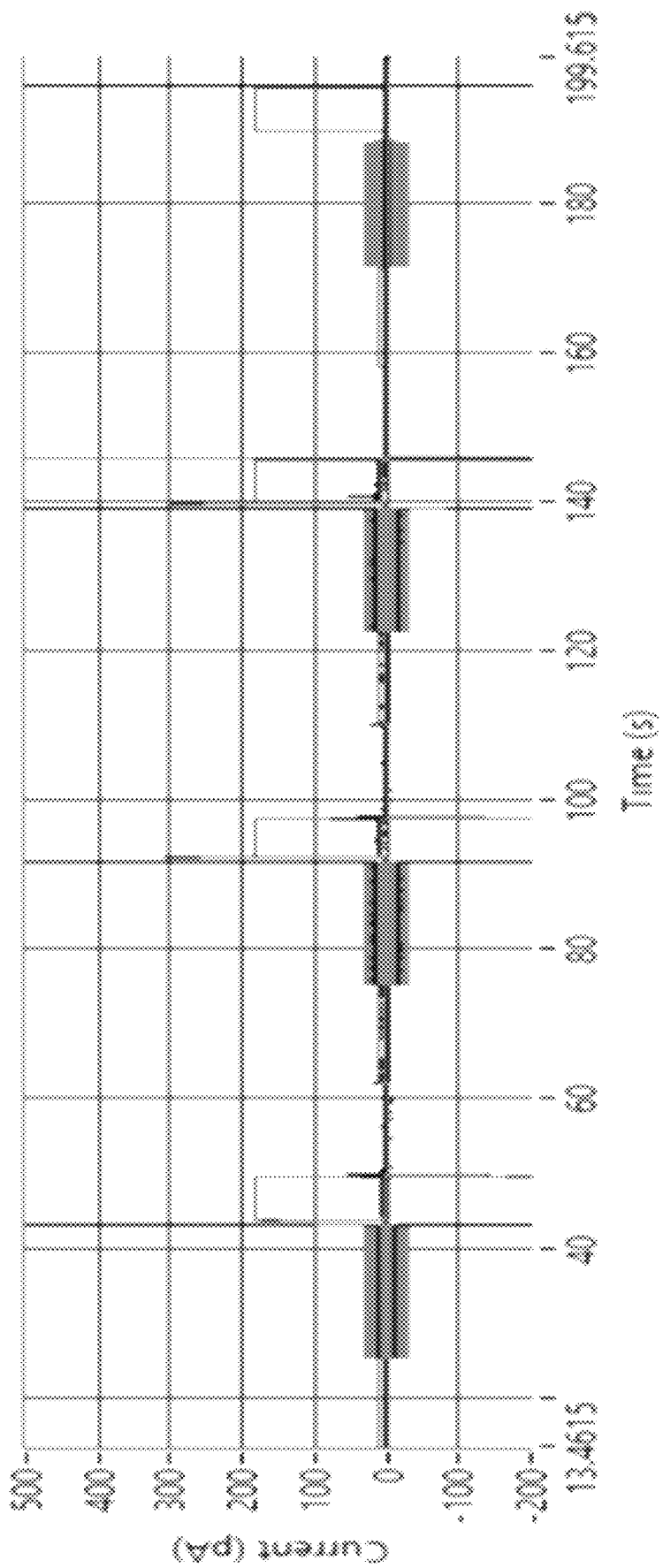
FIGS. 4A and 4B show peptide translocation through single channel of phi29 connector of Channel 304 of MinION.
Figure 4B:
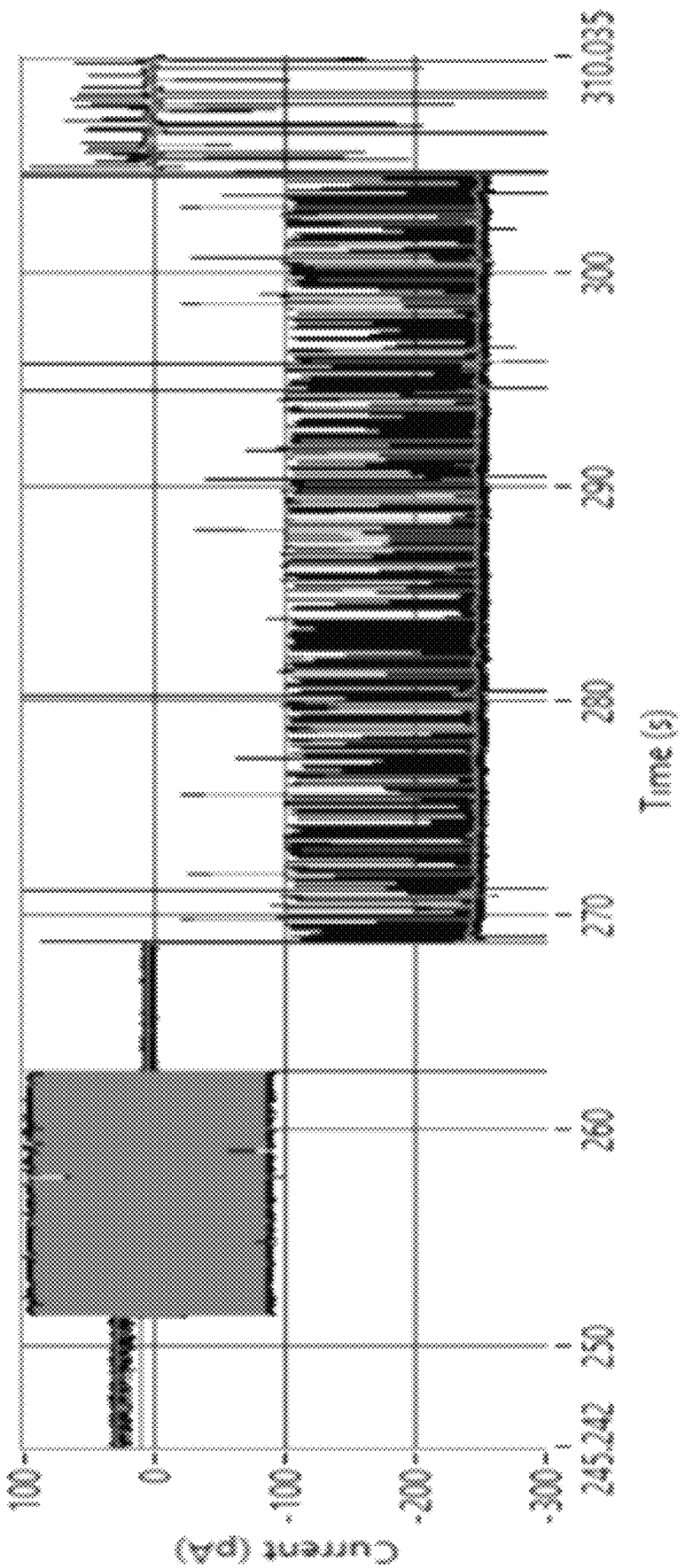

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, biology, and the like, which are within the skill of the art.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise.

Nanopores

Nanopores are disclosed herein that comprise connector protein channels of bacteriophage DNA packaging motors. These nanopores can be incorporated into copolymeric membranes as disclosed herein. Connector protein channels of bacteriophage DNA packaging motors are not membrane proteins. The insertion of motor channel into liposomes and lipid bilayer membranes has been described in the art. But their insertion into copolymer membranes is described herein for the first time. The connector protein channels of bacteriophage DNA packaging motors are first inserted into liposomes. The liposomes can fuse with lipid membranes as previously described. Disclosed herein is the fusion of liposomes comprising the connector protein channels with copolymeric membranes, not lipid membrane. An applied electrical potential across the copolymer membrane results in fusion of the liposomes with the copolymeric membrane. As disclosed herein, the connector protein channels in the liposomes can be inserted into the copolymer membrane such that they form channels across the membrane. As disclosed herein, these channels allow the passage of analytes into and across the copolymer membrane.

The nanopores may be inserted into membranes in a format compatible with a device for analyzing the interactions of analytes with individual nanopores, such as a format in which multiple membranes each comprising a single nanopore are present in an array, wherein the device is set up to detect changes in current flowing through each nanopore individually. The nanopores can be used as sensors for characterizing a target analyte, such as, for example, a polynucleotide or polypeptide. Also disclosed herein are methods of making nanopore sensors from connector protein channels of bacteriophage DNA packaging motors. This use of nanopores allows for high-throughput, simultaneous detection of many types of cancer biomarkers and enables applications such as protein sequencing.

Described herein for the first time is the insertion of connector protein channels of viral DNA packaging motors into copolymeric membranes. The copolymeric membrane is stable at least for a few months and also resistant to higher voltages than lipid bilayers, into which the connector protein channels of viral DNA packaging motors have previously been inserted. In standard methods of inserting pores into copolymeric membranes for use in detector devices, subunits of the pores are suspended in a purified form in a solution containing the copolymeric membrane, for example a triblock copolymer membrane, such that the pore diffuses to the membrane and is inserted by binding to the membrane and assembling into a functional state. However, to insert a nanopore derived from connector protein channels of viral DNA packaging motors into a copolymeric membrane, a liposome into which the nanopore is inserted is fused with the copolymeric membrane under an applied potential.

DNA-Packaging Motor Connector Proteins

The nanopore is derived from a connector protein of a viral DNA packaging motor. The connector protein may be a connector protein of a bacteriophage DNA packaging motor. The connector protein may be a wild-type protein or may be modified compared to the wild-type connector protein. In one embodiment, the modified protein is a truncated version of the connector protein, such as a fragment or portion of the connector protein, and/or the modified protein may comprise additional amino acids at one or both ends of one or more of the subunits of the connector protein, and one may comprise one or more amino acid substitution, deletion or addition within the amino acid sequence of the connector protein.

In some embodiments, the nanopore comprises the aperture forming region of the connector protein. The nanopore may, for example, comprise one or more truncated subunits of the connector protein. In one embodiment, the aperture forming region is modified to alter one or more property of the channel of the nanopore.

In some embodiments, the nanopore comprises a whole connector protein. For example, a connector protein comprising only full length subunits of the connector protein.

In some embodiments, the nanopore is a multimeric protein formed of six or more connector protein subunits, such as 7, 8, 9 10, 11 or 12 subunits. For example, the nanopore may be a dodecameric protein. One or more, such as 2, 3, 4, 5, 6, 7, 8, 9, 10, 11 or 12 of the subunits may be modified. In one embodiment, one or more of the subunits may be modified at the C-terminus and/or N-terminus, such as to increase the hydrophilicity at one or both ends of the nanopore. For example, one or more of the subunits may be modified by the addition of a flexible linker and/or a peptide tag at the C-terminus and/or N-terminus. In some embodiments, the nanopore is composed of identical subunits.

Any suitable linker may be used, such as, for example, a linker comprising from 3 to 12 amino acids, such as from 4 or 5 to 10, preferably 6 to 8 amino acids. The amino acids in the linker may selected from lysine, serine, arginine, proline, glycine and/or alanine. Examples of suitable linkers include, but are not limited to, the following: GGGS, PGGS, PGGG, RPPPPP, RPPPP, VGG, RPPG, PPPP, RPPG, PPPPPPPP, RPPG, GGG, GGGG, GGGGG and GGGGGG.

Any suitable peptide tag may be used to facilitate purification of the connector protein. For example, in one embodiment, the tag may be a strep tag. In one embodiment, the streptag has a length of from 8 to 11 amino acids and/or the streptag amino acid sequence contains the motif HPQ. The streptag may for example comprise or consist of the amino acid sequence WSHPQSEK, WSHPQFEK, NWSHPQFEK, PWSHPQFEK or GGSHPQFEG. This sequence may be varied by addition, deletion or substitution of one or more, such as 2, 3, 4 or 5 of the amino acids, provided that the core "HPQ" motif is maintained. The variant sequence is typically from 8 to 11 amino acids NWSHPQFEK, PWSHPQFEK, and GGSHPQFEG.

An ATP-driven motor of bacteriophage packages the linear dsDNA of the virus into a preformed procapsid. The protein hub of this motor is a truncated cone structure, termed a connector that allows dsDNA to enter during maturation and exit during infection. The connector has a central channel formed by twelve GP10 protein subunits. An exemplary unmodified viral DNA-packaging motor connector protein from bacteriophage phi29 has been purified and its three-dimensional structure has been crystallographically characterized (e.g., Guasch et al., 1998 FEBS Lett. 430:283; Marais et al., 2008 Structure 16:1267). The phi29 channel has a 3.6 nm narrow and a 6 nm wide end, which is larger than most membrane protein channels. Accordingly, a number of preferred embodiments as described herein refer to the phi29 DNA-packaging motor connector protein (e.g., Genbank Acc. No. ACE96033) and/or to polypeptide subunits thereof including fragments, variants and derivatives thereof that are capable of forming a channel (e.g., Acc. Nos. gi 29565762, gi 31072023, gi 66395194, gi 29565739, gi 157738604).

While the connector proteins of viruses share little sequence homology and vary in molecular weight, there is significant underlying structural similarity. In particular, DNA-packaging motor connector proteins of other dsDNA viruses (e.g., T4, lambda, P22, P2, T3, T5 and T7), despite sharing little sequence homology with, and differing in molecular weight from, the phi29 connector, exhibit significant underlying structural similarities (e.g., Bazinet et al., 1985 Ann Rev. Microbiol. 39:109-29).

In certain embodiments the use of an isolated viral DNA-packaging motor connector protein from other dsDNA viruses is contemplated, including without limitation the isolated viral DNA-packaging motor connector protein from any of phage lambda, P2, P3, P22, T3, T4, T5, SPP1, H97 and T7, such as an isolated dsDNA virus DNA-packaging motor connector protein (e.g., T4 (Acc. No. NP—049782)(Driedonks et al., 1981 J Mol Biol 152:641), lambda (Acc. Nos. gi 549295, gi 6723246, gi 15837315, gi 16764273)(Kochan et al., 1984 J Mol Biol 174:433), SPP1

(Acc. No. P54309), P22 (Acc. No. AAA72961)(Cingolani et al., 2002 J Struct Biol 139:46), P2 (Acc. No. NP—046757, P3 (Nutter et al., 1972 J. Viral. 10(3):560-2), T3 (Acc. No. CAA35152)(Carazo et al., 1986 J I. Ultrastruct Mol Struct Res 94:105), T5 (Accession numbers AAX12078, YP-006980; AAS77191; AAU05287), T7 (Acc. No. NP-041995)(Cerritelli et al., 1996 J Mol Biol 285:299; Agirrezabala et al., 2005 J Mol Biol 347:895)).

Without wishing to be bound by theory, it is believed in this regard that like the phi29 DNA-packaging motor connector protein exemplified herein, these and other dsDNA virus packaging motor connector proteins, which have been substantially structurally characterized, can be incorporated into a membrane layer to form an aperture through which conductance can occur when an electrical potential is applied across the membrane in the same manner as the connector protein of the phi29 DNA-packaging motor. Accordingly, disclosure herein with respect to the phi29 connector protein is intended, for certain embodiments, to be illustrative of related embodiments that are contemplated using any of such other isolated dsDNA viral DNA-packaging motor connector proteins.

The connector protein of the phi29 DNA-packaging motor, or the connector protein from another bacteriophage DNA-packaging motor, may be modified according to the teachings found herein.

As described in greater detail herein, isolated DNA-packaging motor connector protein polypeptides, including such polypeptides that have been artificially engineered to possess properties of membrane incorporation (e.g., stable transmembrane integration in a membrane layer) and functional electroconductive transmembrane aperture formation, can be used as electroconductive biosensors for cancer biomarkers.

As described herein, phi29 and other isolated dsDNA viral DNA-packaging motor protein connectors, including engineered and mutated versions thereof, such as fusion proteins, that retain their aperture domain and comprise an affinity domain may be usefully incorporated into membrane layers to form apertures permitting their use as conductive channels when an electrical potential is applied across the membrane.

Modified isolated double-stranded DNA virus DNA-packaging motor protein connectors such as the phi29 connector may be engineered to have desired structures for use in the presently disclosed embodiments, where protein crystallographic structural data are readily available. Procedures for large scale production and purification of phi29 connector have been developed (Guo et al., 2005; Ibanez et al., Nucleic Acids Res. 12, 2351-2365 (1984), Robinson et al., Nucleic Acids Res. 34, 2698-2709 (2006), Xiao et al., ACS Nano 3, 100-107 (2009).

Disclosed for use in the methods and inclusion in the compositions are viral DNA-packaging motor connector protein-derived polypeptides and fusion proteins having amino acid sequence regions that are identical or similar to sequences known in the art, or fragments or portions thereof. For example, by way of illustration and not limitation, a mutant bacteriophage phi29 viral DNA-packaging motor connector protein [e.g., Genbank Acc. No. ACE96033] or an engineered bacteriophage phi29 viral DNA-packaging motor connector protein-derived polypeptide fusion protein is contemplated for use in the disclosed compositions and methods, as are polypeptides having at least 80%, 90%, or 95% similarity to the herein disclosed polypeptides and to portions of such polypeptides, wherein such portions of a mutant or engineered phi29 viral DNA-packaging motor connector protein-derived polypeptide generally contain at least 150, 175, 200, 225, 250, 275, including at least 240, 260, 280, 285, 290, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330 or more amino acids.

In like fashion, certain other embodiments contemplate other mutant double-stranded DNA bacteriophage virus motor connector proteins such as mutated forms of phage T4 DNA-packaging motor connector protein polypeptide, lambda phage DNA-packaging motor connector protein polypeptide (Accession numbers gi549295, gi6723246, gi15837315, gi16764273), phage SPP1 DNA-packaging motor connector protein polypeptide (Accession number P54309), phage P22 DNA-packaging motor connector protein polypeptide (Accession number AAA72961), phage P2 DNA-packaging motor connector protein polypeptide (Accession number NP—046757), phage P3 DNA-packaging motor connector protein polypeptide (Nutter et al., 1972 J. Virol. 10(3):560-2), phage T3 DNA-packaging motor connector protein polypeptide (Accession number CAA35152), phage T5 DNA-packaging motor connector protein polypeptide (Accession numbers AAX12078, YP006980; AAS77191; AAU05287), phage T7 DNA-packaging motor connector protein polypeptide (Accession number NP041995) and phage HK97 DNA-packaging motor connector protein polypeptide (Accesssion number NP_037699). For example, a mutant of any of these bacteriophage viral DNA-packaging motor connector proteins or an engineered version of any of these bacteriophage viral DNA-packaging motor connector proteins, which may be a polypeptide fusion protein, is contemplated for use in the disclosed compositions and methods, as are polypeptides having at least 80%, 90%, or 95% similarity to the herein disclosed polypeptides and to fragments of such polypeptides. A "fragment" of a mutant or engineered viral DNA-packaging motor connector protein-derived polypeptide generally contains at least 150, 175, 200, 225, 250, 275, including at least 240, 260, 280, 285, 290, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330 or more amino acids.

The terms "fragment," "derivative," and "analog" when referring to viral DNA-packaging motor connector proteins or polypeptides, refers to variants of a mutant viral DNA-packaging motor connector protein-derived polypeptide described herein, or a fusion protein comprising such polypeptide, that retains essentially the same biological function or activity as such polypeptide. Thus, an analog includes a proprotein which can be activated by cleavage of the proprotein portion to produce an active viral DNA-packaging motor connector polypeptide, which in preferred embodiments may be incorporated into a membrane layer to form an aperture through which conductance can occur when an electrical potential is applied across the membrane and/or may be capable of self-assembly into a homododecameric viral DNA-packaging motor connector protein such as may form such an aperture to obtain a conductive channel-containing membrane.

A fragment, derivative or analog of a viral DNA-packaging motor connector protein-derived polypeptide described herein, including polypeptides or fusion proteins or domains or fragments thereof may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which additional amino acids are fused to the mutant viral DNA-packaging motor connector protein-derived polypeptide, including amino acids that are employed for detection or specific functional alteration of the mutant or engineered viral DNA-packaging motor connector protein-derived polypeptide or a proprotein sequence. Such fragments, derivatives and analogs are deemed to be within the scope of those skilled in the art from the teachings herein.

As known in the art "similarity" between two polypeptides is determined by comparing the amino acid sequence and conserved amino acid substitutes thereto of the polypeptide to the sequence of a second polypeptide. Fragments of the nucleic acids encoding polypeptides according to the presently disclosed embodiments may be used to synthesize full-length nucleic acids encoding a mutant or engineered viral DNA-packaging motor connector protein-derived polypeptide. As used herein, "% identity" refers to the percentage of identical amino acids situated at corresponding amino acid residue positions when two or more polypeptide are aligned and their sequences analyzed using a gapped BLAST algorithm (e.g., Altschul et al., 1997 Nucl. Ac. Res. 25:3389) which weights sequence gaps and sequence mismatches according to the default weightings provided by the National Institutes of Health/NCBI database (National Center for Biotechnology Information, Bethesda, Md.).

The term "isolated" means that the material is removed from its original environment (e.g., the natural environment if it is naturally occurring). For example, a naturally occurring nucleic acid or polypeptide present in a living animal or intact naturally occurring virus is not isolated, but the same nucleic acid or polypeptide, separated from some or all of the co-existing materials in the natural system, is isolated. Such nucleic acids could be part of a vector and/or such nucleic acids or polypeptides could be part of a composition, and still be isolated in that such vector or composition is not part of its natural environment. Methods of isolating connector proteins of bacteriophage motor proteins are known in the art. The connector proteins of bacteriophage motor proteins for use in the methods and compositions described herein can be produced recombinantly used methods well known in the art.

The term "gene" means the segment of DNA involved in producing a polypeptide chain; it includes regions preceding and following the coding region "leader and trailer" as well as intervening sequences (introns) between individual coding segments (exons).

Polymeric Membranes

Any polymeric membrane may be used in accordance with the invention. Suitable polymeric membranes are well-known in the art. The membrane is preferably an amphiphilic layer. An amphiphilic layer is a layer formed from amphiphilic molecules, such as phospholipids, which have both at least one hydrophilic portion and at least one lipophilic or hydrophobic portion. Block copolymers are polymeric materials in which two or more monomer sub-units are polymerized together to create a single polymer chain. Block copolymers typically have properties that are contributed by each monomer sub-unit. However, a block copolymer may have unique properties that polymers formed from the individual sub-units do not possess. Block copolymers can be engineered such that one of the monomer sub-units is hydrophobic (i.e. lipophilic), whilst the other sub-unit(s) are hydrophilic whilst in aqueous media. In this case, the block copolymer may possess amphiphilic properties and may form a structure that mimics a biological membrane. The block copolymer may be a diblock (consisting of two monomer sub-units), but may also be constructed from more than two monomer sub-units to form more complex arrangements that behave as amphiphiles. The copolymer may be a triblock, tetrablock or pentablock copolymer.

In some embodiments, the copolymeric membrane is an amphiphilic ABA type tri-block copolymer membrane. A particularly stable membrane of ABA molecules is described in WO2014064444A1, which is incorporated by reference in its entirety for the teaching of these membranes and their use in forming nanopore sequences.

The amphiphilic molecules may be synthetic or naturally occurring. Non-naturally occurring amphiphiles and amphiphiles which form a monolayer are known in the art and include, for example, block copolymers (Gonzalez-Perez et al., Langmuir, 2009, 25, 10447-10450). Block copolymers are polymeric materials in which two or more monomer sub-units that are polymerized together to create a single polymer chain. Block copolymers typically have properties that are contributed by each monomer sub-unit. However, a block copolymer may have unique properties that polymers formed from the individual sub-units do not possess. Block copolymers can be engineered such that one of the monomer sub-units is hydrophobic (i.e. lipophilic), whilst the other sub-unit(s) are hydrophilic whilst in aqueous media. In this case, the block copolymer may possess amphiphilic properties and may form a structure that mimics a biological membrane. The block copolymer may be a diblock (consisting of two monomer sub-units), but may also be constructed from more than two monomer sub-units to form more complex arrangements that behave as amphiphiles. The copolymer may be a triblock, tetrablock or pentablock copolymer. The membrane is preferably a triblock copolymer membrane.

Archaebacterial bipolar tetraether lipids are naturally occurring lipids that are constructed such that the lipid forms a monolayer membrane. These lipids are generally found in extremophiles that survive in harsh biological environments, thermophiles, halophiles and acidophiles. Their stability is believed to derive from the fused nature of the final bilayer. It is straightforward to construct block copolymer materials that mimic these biological entities by creating a triblock polymer that has the general motif hydrophilic-hydrophobic-hydrophilic. This material may form monomeric membranes that behave similarly to lipid bilayers and encompass a range of phase behaviours from vesicles through to laminar membranes. Membranes formed from these triblock copolymers hold several advantages over biological lipid membranes. Because the triblock copolymer is synthesised, the exact construction can be carefully controlled to provide the correct chain lengths and properties required to form membranes and to interact with pores and other proteins.

Block copolymers may also be constructed from sub-units that are not classed as lipid sub-materials; for example a hydrophobic polymer may be made from siloxane or other non-hydrocarbon based monomers. The hydrophilic sub-section of block copolymer can also possess low protein binding properties, which allows the creation of a membrane that is highly resistant when exposed to raw biological samples. This head group unit may also be derived from non-classical lipid head-groups.

Triblock copolymer membranes also have increased mechanical and environmental stability compared with biological lipid membranes, for example a much higher operational temperature or pH range. The synthetic nature of the block copolymers provides a platform to customise polymer based membranes for a wide range of applications.

The membrane is most preferably one of the membranes disclosed in International Application No. WO2014/064443 or WO2014/064444, which are hereby incorporated herein by reference in entirety.

The amphiphilic molecules may be chemically-modified or functionalised to facilitate coupling of the polynucleotide. The amphiphilic layer may be a monolayer or a bilayer. The amphiphilic layer is typically planar. The amphiphilic layer may be curved. The amphiphilic layer may be supported.

Amphiphilic membranes are typically naturally mobile, essentially acting as two dimensional fluids with lipid diffusion rates of approximately $10^{-8}$ cm s-1. This means that the pore and coupled polynucleotide can typically move within an amphiphilic membrane.

The copolymeric membrane may, in some embodiments, comprise one or more additives, for example to affect the properties of the layer. Suitable additives include, but are not limited to, fatty acids, such as palmitic acid, myristic acid and oleic acid; fatty alcohols, such as palmitic alcohol, myristic alcohol and oleic alcohol; sterols, such as cholesterol, ergosterol, lanosterol, sitosterol and stigmasterol; lysophospholipids, such as 1-Acyl-2-Hydroxy-sn-Glycero-3-Phosphocholine; and ceramides. The copolymeric membrane may, for example, comprise the lipids that were components of the liposome that was fused with the copolymeric membrane to insert the nanopore into the membrane.

The copolymeric membrane may be comprised in a solid state layer. Solid state layers can be formed from both organic and inorganic materials including, but not limited to, microelectronic materials, insulating materials such as $Si_3N_4$, $Al_2O_3$, and SiO, organic and inorganic polymers such as polyamide, plastics such as Teflon® or elastomers such as two-component addition-cure silicone rubber, and glasses. The solid state layer may be formed from graphene. Suitable graphene layers are disclosed in WO 2009/035647. The copolymeric membrane may, for example, be contained within a hole, well, gap, channel, trench or slit within the solid state layer. The skilled person can prepare suitable solid state/copolymeric membrane hybrid systems. Suitable systems are disclosed in WO 2009/020682 and WO 2012/005857 which are hereby incorporated herein by reference in entirety.

Incorporation of Nanopores into Polymer Membranes

The presently described conductive channel-containing membrane may be formed by first incorporating the isolated viral DNA-packaging motor connector protein as provided herein into a liposome, which may then donate membrane-integrated connectors to polymeric membrane systems by way of artificial membrane fusion manipulations.

As used herein, the term "liposome" refers to a lipid vesicle having at least one lipid bilayer. Liposomes are most often composed of phospholipids, especially phosphatidylcholine, but may also include other lipids. Examples of liposomes include multilamellar vesicle (MLV, with several lamellar phase lipid bilayers), small unilamellar liposome vesicle (SUV, with one lipid bilayer), large unilamellar vesicle (LUV), and the cochleate vesicle. Another form of liposome is a multivesicular liposome in which one vesicle contains one or more smaller vesicles. Liposomes can be prepared by disrupting biological membranes (such as by sonication). Liposomes can also be created by sonicating a dispersion of amphipatic lipids, such as phospholipids, in water. Another option is the Mozafari method, which involves the use of heat to form the liposomes, while stirring is used to facilitate homogeneous distribution of the ingredients.

In the disclosed methods, the nanopore is first inserted into liposomes. The liposomes may, for example, be stable, giant and/or unilamellar liposomes.

Liposomes can, for example, be formed by sonication, extrusion or the Mozafari method (Colas et al. (2007) Micron 38:841-847).

The liposome may comprise a lipid bilayer. A lipid bilayer is formed from two opposing layers of lipids. The two layers of lipids are arranged such that their hydrophobic tail groups face towards each other to form a hydrophobic interior. The hydrophilic head groups of the lipids face outwards towards the aqueous environment on each side of the bilayer. The bilayer may be present in a number of lipid phases including, but not limited to, the liquid disordered phase (fluid lamellar), liquid ordered phase, solid ordered phase (lamellar gel phase, interdigitated gel phase) and planar bilayer crystals (lamellar sub-gel phase, lamellar crystalline phase).

Any lipid composition that forms a lipid bilayer may be used. The lipid composition is chosen such that a lipid bilayer having the required properties, such surface charge, ability to support membrane proteins, packing density or mechanical properties, is formed. The lipid composition can comprise one or more different lipids. For instance, the lipid composition can contain up to 100 lipids. The lipid composition preferably contains 1 to 10 lipids. The lipid composition may comprise naturally-occurring lipids and/or artificial lipids.

The lipids typically comprise a head group, an interfacial moiety and two hydrophobic tail groups which may be the same or different. Suitable head groups include, but are not limited to, neutral head groups, such as diacylglycerides (DG) and ceramides (CM); zwitterionic head groups, such as phosphatidylcholine (PC), phosphatidylethanolamine (PE) and sphingomyelin (SM); negatively charged head groups, such as phosphatidylglycerol (PG); phosphatidylserine (PS), phosphatidylinositol (PI), phosphatic acid (PA) and cardiolipin (CA); and positively charged headgroups, such as trimethylammonium-Propane (TAP). Suitable interfacial moieties include, but are not limited to, naturally-occurring interfacial moieties, such as glycerol-based or ceramide-based moieties. Suitable hydrophobic tail groups include, but are not limited to, saturated hydrocarbon chains, such as lauric acid (n-Dodecanolic acid), myristic acid (n-Tetradecononic acid), palmitic acid (n-Hexadecanoic acid), stearic acid (n-Octadecanoic) and arachidic (n-Eicosanoic); unsaturated hydrocarbon chains, such as oleic acid (cis-9-Octadecanoic); and branched hydrocarbon chains, such as phytanoyl. The length of the chain and the position and number of the double bonds in the unsaturated hydrocarbon chains can vary. The length of the chains and the position and number of the branches, such as methyl groups, in the branched hydrocarbon chains can vary. The hydrophobic tail groups can be linked to the interfacial moiety as an ether or an ester. The lipids may be mycolic acid.

The lipids can also be chemically-modified. The head group or the tail group of the lipids may be chemically-modified. Suitable lipids whose head groups have been chemically-modified include, but are not limited to, PEG-modified lipids, such as 1,2-Diacyl-sn-Glycero-3-Phosphoethanolamine-N-[Methoxy(Polyethylene glycol)-2000]; functionalised PEG Lipids, such as 1,2-Distearoyl-sn-Glycero-3 Phosphoethanolamine-N-[Biotinyl(Polyethylene Glycol)2000]; and lipids modified for conjugation, such as 1,2-Dioleoyl-sn-Glycero-3-Phosphoethanolamine-N-(succinyl) and 1,2-Dipalmitoyl-sn-Glycero-3-Phosphoethanolamine-N-(Biotinyl). Suitable lipids whose tail groups have been chemically-modified include, but are not limited to, polymerisable lipids, such as 1,2-bis(10,12-tricosadiynoyl)-sn-Glycero-3-Phosphocholine; fluorinated lipids, such as 1-Palmitoyl-2-(16-Fluoropalmitoyl)-sn-Glycero-3-Phosphocholine; deuterated lipids, such as 1,2-Dipalmitoyl-D62-sn-Glycero-3-Phosphocholine; and ether linked lipids, such as 1,2-Di-O-phytanyl-sn-Glycero-3-Phosphocholine. The lipids may be chemically-modified or functionalised to facilitate coupling of the polynucleotide.

The lipid composition, typically comprises one or more additives that will affect the properties of the layer. Suitable additives include, but are not limited to, fatty acids, such as palmitic acid, myristic acid and oleic acid; fatty alcohols, such as palmitic alcohol, myristic alcohol and oleic alcohol; sterols, such as cholesterol, ergosterol, lanosterol, sitosterol and stigmasterol; lysophospholipids, such as 1-Acyl-2-Hydroxy-sn-Glycero-3-Phosphocholine; and ceramides.

In some embodiments, the method involves incorporating connector protein channels of bacteriophage DNA packaging motors into liposomes, contacting a copolymeric membrane with the liposomes, and inducing liposome-polymer fusion by application of voltage across the copolymer membrane. In one embodiment the applied potential is from 50 mV to 500 mV, from 100 mV to 360 mV, from 200 mV to 400 mV, from 300 mV to 350 mV, or from 300 mV to 325 mV. Any suitable method of controlling the insertion of a nanopore in a membrane using voltage control can be used. Voltage assisted pore insertion is known and is described in U.S. Pat. No. 9,797,013 and WO 2018/096348, hereby incorporated herein by reference in their entirety. MinKNOW is a software package provided by Oxford Nanopore Technologies Ltd which is used and referenced in the methods described herein to apply a potential difference across the membrane and facilitate pore insertion. In methods of voltage assisted pore insertion, an initial voltage may be applied and then increased gradually or stepped up over time up to a final voltage. In one embodiment, an initial voltage is applied (e.g., from 50 to 100 mV) and voltage is increased by 5 mV every 10 s, up to a voltage of 500 mV. In another embodiment, an initial voltage is applied (e.g., from 50 to 100 mV) and voltage is increased by 5 mV every 10 s, up to a voltage of 360 mV.

Liposomes can be prepared with dried DPHPC (1,2-diphytanoyl-sn-glycero-3-phosphocholine). Purified connector protein and rehydration buffer can be added to the prepared liposomes. The resulting solution contains liposomes containing connector proteins. These liposomes can then be used to insert connector proteins into a copolymeric membrane by liposome fusion.

Methods of Characterizing an Analyte

Also disclosed are methods of characterizing a target analyte using the disclosed nanopores. The method comprises contacting the target analyte with a disclosed nanopore system such that the target analyte moves through the nanopore. One or more characteristics of the target analyte are then measured as the analyte moves with respect to the nanopore using standard methods known in the art. One or more characteristics of the target analyte are preferably measured as the analyte moves through the nanopore. These steps can be carried out with a potential applied across the nanopore. For example, the applied potential may be a voltage potential, a chemical potential, or an electrical potential. An example of a chemical potential is a salt gradient across an amphiphilic layer.

A variety of different types of measurements may be made. This includes without limitation: electrical measurements and optical measurements. Possible electrical measurements include: current measurements, impedance measurements, tunnelling measurements (Ivanov A P et al., Nano Lett. 2011 Jan. 12; 11(1):279-85), and FET measurements (WO 2005/124888). Optical measurements may be combined with electrical measurements (Soni G V et al., Rev Sci Instrum. 2010 January; 81(1):014301). The measurement may be a transmembrane current measurement such as measurement of ionic current flowing through the pore. In some cases, measurement is done with a field-effect-transistor (FET) nanopore sensor. In some cases, measurement is done with integrated tunneling electrodes.

In some embodiments, the method involves measuring the current passing through the nanopore as the analyte moves with respect to the nanopore wherein the current is indicative of one or more characteristics of the target analyte and thereby characterizing the target analyte. In some embodiments, the target analyte is a target polynucleotide and the method involves contacting the target polynucleotide with the disclosed nanopore present in a copolymer membrane and a polynucleotide binding protein such that the protein controls the movement of the target polynucleotide through the nanopore, and then measuring the current passing through the nanopore as the polynucleotide moves with respect to the nanopore wherein the current is indicative of one or more characteristics of the target polynucleotide and thereby characterizing the target polynucleotide The disclosed method can be used to characterize a target analyte. In some embodiments, the target analyte is a metal ion, an inorganic salt, a polymer, an amino acid, a peptide, a polypeptide, a protein, a nucleotide, an oligonucleotide, a polynucleotide, a dye, a bleach, a pharmaceutical, a diagnostic agent, a recreational drug, an explosive, or an environmental pollutant. In some embodiments, the analyte is an amino acid, a peptide, a polypeptide and/or a protein. The amino acid, peptide, polypeptide, or protein can be naturally-occurring or non-naturally-occurring. The polypeptide or protein can include within them synthetic or modified amino acids. A number of different types of modification to amino acids are known in the art. The protein can be an enzyme, an antibody, a hormone, a growth factor, or a growth regulatory protein, such as a cytokine. The cytokine may be selected from interleukins, such as IFN-1, IL-1, IL-2, IL-4, IL-5, IL-6, IL-10, IL-12 and IL-13, interferons, such as IL-γ, and other cytokines, such as TNF-α. The protein may be a bacterial protein, a fungal protein, a virus protein, or a parasite-derived protein.

The target analyte can be a nucleotide, an oligonucleotide, or a polynucleotide. The disclosed method can involve measuring one or more characteristics selected from (i) the length of the target polynucleotide, (ii) the identity of the target polynucleotide, (iii) the sequence of the target polynucleotide, (iv) the secondary structure of the target polynucleotide and (v) whether or not the target polynucleotide is modified.

A nucleotide typically contains a nucleobase, a sugar and at least one phosphate group. The nucleobase is typically heterocyclic. Nucleobases include, but are not limited to, purines and pyrimidines and more specifically adenine, guanine, thymine, uracil and cytosine. The sugar is typically a pentose sugar. Nucleotide sugars include, but are not limited to, ribose and deoxyribose. The nucleotide is typically a ribonucleotide or deoxyribonucleotide. The nucleotide typically contains a monophosphate, diphosphate or triphosphate. Phosphates may be attached on the 5' or 3' side of a nucleotide. Nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), 5-methylcytidine monophosphate, 5-methylcytidine diphosphate, 5-methylcytidine triphosphate, 5-hydroxymethylcytidine monophosphate, 5-hydroxymethylcytidine diphosphate, 5-hydroxymethylcytidine triphosphate, cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP), 5-methyl-2'-deoxycytidine monophosphate, 5-methyl-2'-deoxycytidine diphosphate, 5-methyl-2'-deoxycytidine triphosphate, 5-hydroxymethyl-2'-deoxycytidine monophosphate, 5-hydroxymethyl-2'-deoxycytidine diphosphate and 5-hydroxymethyl-2'-deoxycytidine triphosphate. The nucleotides are preferably selected from AMP, TMP, GMP, UMP, dAMP, dTMP, dGMP or dCMP. The nucleotides may be abasic (i.e. lack a nucleobase). The nucleotides may contain additional modifications. In particular, suitable modified nucleotides include, but are not limited to, 2'amino pyrimidines (such as 2'-amino cytidine and 2'-amino uridine), 2'-hyrdroxyl purines (such as, 2'-fluoro pyrimidines (such as 2'-fluorocytidine and 2'fluoro uridine), hydroxyl pyrimidines (such as 5'-α-P-borano uridine), 2'-O-methyl nucleotides (such as 2'-O-methyl adenosine, 2'-O-methyl guanosine, 2'-O-methyl cytidine and 2'-O-methyl uridine), 4'-thio pyrimidines (such as 4'-thio uridine and 4'-thio cytidine) and nucleotides have modifications of the nucleobase (such as 5-pentynyl-2'-deoxy uridine, 5-(3-aminopropyl)-uridine and 1,6-diaminohexyl-N-5-carbamoylmethyl uridine). Oligonucleotides are short nucleotide polymers which typically have 50 or fewer nucleotides, such 40 or fewer, 30 or fewer, 20 or fewer, 10 or fewer or 5 or fewer nucleotides. The oligonucleotides may comprise any of the nucleotides discussed above, including the abasic and modified nucleotides.

The polynucleotide may be single stranded or double stranded. In some cases, at least a portion of the polynucleotide is double stranded. A single stranded polynucleotide may have one or more primers hybridized thereto and hence comprise one or more short regions of double stranded polynucleotide. The primers may be the same type of polynucleotide as the target polynucleotide or may be a different type of polynucleotide.

The polynucleotide can be a nucleic acid, such as deoxyribonucleic acid (DNA) or ribonucleic acid (RNA). The target polynucleotide can comprise one strand of RNA hybridized to one strand of DNA. The polynucleotide may be any synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains.

The whole or only part of the target polynucleotide may be characterized using this method. The target polynucleotide can be any length. For example, the polynucleotide can be at least 10, at least 50, at least 100, at least 150, at least 200, at least 250, at least 300, at least 400 or at least 500 nucleotide pairs in length. The polynucleotide can be 1000 or more nucleotide pairs, 5000 or more nucleotide pairs in length or 100000 or more nucleotide pairs in length.

The disclosed method is typically carried out on a sample that is known to contain or suspected to contain the target analyte. Alternatively, the method may be carried out on a sample to confirm the identity of one or more target analytes whose presence in the sample is known or expected. In some embodiments, the sample is a biological sample. The method may be carried out in vitro on a sample obtained from or extracted from any organism or microorganism. The organism or microorganism is typically archaean, prokaryotic or eukaryotic and typically belongs to one the five kingdoms: plantae, animalia, fungi, monera and protista. The method may be carried out in vitro on a sample obtained from or extracted from any virus. The sample can in some embodiments be a fluid sample, such as a body fluid of a patient. For example, the sample can be blood, plasma, serum, urine, lymph, saliva, or amniotic fluid. Typically, the sample is human in origin, but alternatively it may be from another mammal animal such as from commercially farmed animals such as horses, cattle, sheep or pigs or may alternatively be pets such as cats or dogs. Alternatively, a sample of plant origin can be obtained from a commercial crop, such as a cereal, legume, fruit or vegetable, for example wheat, barley, oats, canola, maize, soya, rice, bananas, apples, tomatoes, potatoes, grapes, tobacco, beans, lentils, sugar cane, cocoa, cotton.

The sample may also be an environmental sample. For example, the sample can be a water sample, such as drinking water, sea water, or river water.

The sample is typically processed prior to being assayed, for example by centrifugation or by passage through a membrane that filters out unwanted molecules or cells. The sample may be measured immediately upon being taken. The sample may also be typically stored prior to assay, e.g. below −70° C.

In strand sequencing, the DNA is translocated through the nanopore either with or against an applied potential. Exonucleases that act progressively or processively on double stranded DNA can be used on the cis side of the nanopore to feed the remaining single strand through under an applied potential or the trans side under a reverse potential. Likewise, a helicase that unwinds the double stranded DNA can also be used in a similar manner. A polymerase may also be used. There are also possibilities for sequencing applications that require strand translocation against an applied potential, but the DNA must be first "caught" by the enzyme under a reverse or no potential. With the potential then switched back following binding the strand will pass cis to trans through the nanopore and be held in an extended conformation by the current flow. The single strand DNA exonucleases or single strand DNA dependent polymerases can act as molecular motors to pull the recently translocated single strand back through the pore in a controlled stepwise manner, trans to cis, against the applied potential.

In some embodiments, the method of characterizing a target polynucleotide involves contacting the target sequence with the disclosed nanopore and a helicase enzyme. Any helicase may be used in the method. Helicases may work in two modes with respect to the pore. First, the method is preferably carried out using a helicase such that it moves the target sequence through the pore with the field resulting from the applied voltage. In this mode the 5' end of the DNA is first captured in the nanopore, and the enzyme moves the DNA into the nanopore such that the target sequence is passed through the nanopore with the field until it finally translocates through to the trans side of the bilayer. Alternatively, the method is preferably carried out such that a helicase enzyme moves the target sequence through the nanopore against the field resulting from the applied voltage. In this mode the 3' end of the DNA is first captured in the nanopore, and the enzyme moves the DNA through the pore such that the target sequence is pulled out of the nanopore against the applied field until finally ejected back to the cis side of the bilayer.

In exonuclease sequencing, an exonuclease releases individual nucleotides from one end of the target polynucleotide and these individual nucleotides are identified. In another embodiment, the method of characterizing a target polynucleotide involves contacting the target sequence with a disclosed nanopore and an exonuclease enzyme. Any of the exonuclease enzymes discussed above may be used in the method. The enzyme may be covalently attached to the nanopore as discussed above.

Exonucleases are enzymes that typically latch onto one end of a polynucleotide and digest the sequence one nucleotide at a time from that end. The exonuclease can digest the polynucleotide in the 5' to 3' direction or 3' to 5' direction. The end of the polynucleotide to which the exonuclease binds is typically determined through the choice of enzyme used and/or using methods known in the art. Hydroxyl groups or cap structures at either end of the polynucleotide may typically be used to prevent or facilitate the binding of the exonuclease to a particular end of the polynucleotide.

The method can involve contacting the polynucleotide with the exonuclease so that the nucleotides are digested from the end of the polynucleotide at a rate that allows characterization or identification of a proportion of nucleotides as discussed above. Methods for doing this are well known in the art. For example, Edman degradation is used to successively digest single amino acids from the end of polypeptide such that they may be identified using High Performance Liquid Chromatography (HPLC). A homologous method may be used in the present methods.

The rate at which the exonuclease functions is typically slower than the optimal rate of a wild-type exonuclease. A suitable rate of activity of the exonuclease in the disclosed method involves digestion of from 0.5 to 1000 nucleotides per second, from 0.6 to 500 nucleotides per second, 0.7 to 200 nucleotides per second, from 0.8 to 100 nucleotides per second, from 0.9 to 50 nucleotides per second or 1 to 20 or 10 nucleotides per second. The rate is preferably 1, 10, 100, 500 or 1000 nucleotides per second. A suitable rate of exonuclease activity can be achieved in various ways. For example, variant exonucleases with a reduced optimal rate of activity may be used.

The disclosed methods may be carried out using any apparatus that is suitable for investigating a membrane/pore system in which a nanopore is inserted into a copolymer membrane. The methods may involve measuring the current passing through the nanopore as the analyte, such as a target polynucleotide, moves with respect to the nanopore. Therefore the apparatus may also comprise an electrical circuit capable of applying a potential and measuring an electrical signal across the membrane and nanopore. The methods may be carried out using a patch clamp or a voltage clamp.

The disclosed methods may involve measuring of a current passing through the nanopore as the analyte, such as a target polynucleotide, moves with respect to the nanopore. Suitable conditions for measuring ionic currents through transmembrane protein nanopore are known in the art. The voltage used is typically from +2 V to −2 V, typically −400 mV to +400 mV. The voltage used can be in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used can be in the range 100 mV to 240 mV, such as 120 mV to 220 mV. It is possible to increase discrimination between different nucleotides by a nanopore by using an increased applied potential.

The methods are typically carried out in the presence of charge carriers, such as metal salts, for example alkali metal salt, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or 1-ethyl-3-methyl imidazolium chloride. In the exemplary apparatus discussed above, the salt is present in the aqueous solution in the chamber. Potassium chloride (KCl), sodium chloride (NaCl) or caesium chloride (CsCl) is typically used. KCl is preferred. The salt concentration may be at saturation. The salt concentration may be 3M or lower and is typically from 0.1 to 2.5 M, from 0.3 to 1.9 M, from 0.5 to 1.8 M, from 0.7 to 1.7 M, from 0.9 to 1.6 M or from 1 M to 1.4 M. The salt concentration can be from 150 mM to 1 M. The method can be carried out using a salt concentration of at least 0.3 M, such as at least 0.4 M, at least 0.5 M, at least 0.6 M, at least 0.8 M, at least 1.0 M, at least 1.5 M, at least 2.0 M, at least 2.5 M or at least 3.0 M. High salt concentrations provide a high signal to noise ratio and allow for currents indicative of the presence of a nucleotide to be identified against the background of normal current fluctuations.

The methods can be carried out in the presence of a buffer. In the exemplary apparatus discussed above, the buffer is present in the aqueous solution in the chamber. Any suitable buffer may be used in the method. Typically, the buffer is HEPES. Another suitable buffer is Tris-HCl buffer. The methods are typically carried out at a pH of from 4.0 to 12.0, from 4.5 to 10.0, from 5.0 to 9.0, from 5.5 to 8.8, from 6.0 to 8.7 or from 7.0 to 8.8 or 7.5 to 8.5.

The methods may be carried out at a temperature from 0° C. to 100° C., from 15° C. to 95° C., from 16° C. to 90° C., from 17° C. to 85° C., from 18° C. to 80° C., 19° C. to 70° C., or from 20° C. to 60° C. The methods can be carried out at room temperature. The methods are optionally carried out at a temperature that supports enzyme function, such as about 37° C.

The method can be carried out in the presence of free nucleotides or free nucleotide analogues and an enzyme cofactor that facilitate the action of the polynucleotide binding protein, such as a helicase or an exonuclease. The free nucleotides may be one or more of any of the individual nucleotides discussed above. The free nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP). The enzyme cofactor is a factor that allows the helicase to function. The enzyme cofactor is in some embodiments a divalent metal cation, such as $Mg^{2+}$, $Mn^{2+}$, $Ca^{2+}$ or $Co^{2+}$.

Also disclosed herein is a kit for characterizing, such as sequencing, a target polynucleotide. The kit comprises a nanopore system disclosed herein and a polynucleotide binding protein, such as a helicase or an exonuclease. The disclosed kits ay additionally comprise one or more other reagents or instruments which enable any of the embodiments mentioned above to be carried out. Such reagents or instruments include one or more of the following: suitable buffer(s) (aqueous solutions), means to obtain a sample from a subject (such as a vessel or an instrument comprising a needle), means to amplify and/or express polynucleotide sequences or voltage or patch clamp apparatus. The kit may also, optionally, comprise instructions to enable the kit to be used in the disclosed methods or details regarding which patients the method may be used for. The kit may, optionally, comprise nucleotides.

Also disclosed herein is an apparatus for characterizing, such as sequencing, target polynucleotides in a sample. The apparatus may comprise a copolymer membrane containing plurality of nanopores disclosed herein and a plurality of polynucleotide binding proteins, such as helicases or exonucleases. The apparatus may be any conventional apparatus for analyte analysis, such as an array or a chip. In some embodiments, the apparatus may be any of those described in WO 2010/122293, WO2011067559, or WO 2000/028312 which are hereby incorporated herein by reference in entirety.

In particular, a device comprising an array of copolymeric membranes that comprise a nanopore derived from a connector protein of a bacteriophage DNA packaging motor is disclosed. The device may further comprise a means for applying a voltage potential across the membranes and a means for detecting electrical changes across the membranes. The device may comprise multiple channels, wherein each channel comprises a copolymeric membrane into which is inserted a nanopore derived from a connector protein of a bacteriophage DNA packaging motor, and a means for applying a voltage potential across the membranes and a means for detecting electrical changes across the membrane. The device may further comprise a fluidics system configured to controllably supply a sample to be characterized to the membranes.

The following are various aspects of an invention disclosed herein:
1. The insertion of the connector protein channel of bacteriophage phi29, T3, T4, T5, T7, SPP1, and HK97 DNA packaging motor into the MinION from Oxford Nanopore Technologies.
2. The insertion of the connector protein channel of bacteriophage phi29, T3, T4, T5, T7, SPP1, and HK97 DNA packaging motor into the MinION polymer membrane via a two-step approach: the first step is the insertion of the connector protein into liposome and the second step is the fusion of the liposome with the polymer membrane in the MinION.
3. The method to confirm phi29 channel insertion into MinION by observation of three-step channel gating.
4. The use of MinION chips containing the connector protein channel of bacteriophage phi29, T3, T4, T5, T7, SPP1, and HK97 DNA packaging motor for high throughput DNA sequencing.
5. The use of MinION chips containing the connector protein channel of bacteriophage phi29, T3, T4, T5, T7, SPP1, and HK97 DNA packaging motor for RNA sequencing.
6. The use of MinION chips containing the connector protein channel of bacteriophage phi29, T3, T4, T5, T7, SPP1, and HK97 DNA packaging motor for detection of antigen, antibody, and phage displaying peptide for the diagnosis of cancer, viral infection, bacterial infection, and other diseases.
7. The use of MinION chips containing the connector protein channel of bacteriophage phi29, T3, T4, T5, T7, SPP1, and HK97 DNA packaging motor for detection of miRNA for the diagnosis of cancer and other diseases.

A number of embodiments of the invention have been described. Nevertheless, it will be understood that various modifications may be made without departing from the spirit and scope of the invention. Accordingly, other embodiments are within the scope of the following claims.

EXAMPLES

Example 1: Insertion of the Connector Protein Channel of Bacteriophage Phi29 DNA Packaging Motor into Copolymeric Membranes FIGS. 1 to 4 show insertion of the connector protein channel of bacteriophage phi29 DNA packaging motor into copolymeric membranes for use with the MinION device. The following methods are equally applicable to other connector protein channels described herein, e.g., phage P2, P3, P22, T3, T4, T5, SPP1, H97, T7, G20c and lambda.

Material and Methods:

Phi29 Protein Purification Methods:

The cloning, expression and purification of phi29 connector was described in previous publications (Hague et al., 2013, Nat. Protoc., 8, 373-392; Wendell et al., 2009, Nat. Nanotechnol., 4, 765-772). In brief, the constructed plasmid containing the gene 10 (gp10) encoding a single subunit of the phi29 connector protein channel was transformed to *E. coli* HMS 174 (DE3) or BL21 (DE3). The *E. coli* containing the plasmid for phi29 was cultured in 500 mL Luria Broth medium at 37° C. until $OD_{600}$ reached 0.5-0.6. The phi29 protein expression was induced by IPTG (final concentration: 0.5 mM) for an additional 3 hours before harvest. The pellets were resuspended in buffer (Tris-HCl 0.1 M, NaCl 0.5 M, ATP 10 mM, Glycerol 14.4%, Imidazole 5 mM) and the cells were lysed. The soluble protein was recovered and collected by centrifugation and passed through a 0.45 µm membrane filter before loading to purification column (Thermo Fisher Scientific) filled by His•Bind® resin (EMD Millipore). The phi29 connector protein channel was eluted using elution buffer (Tris-HCl 0.1 M, NaCl 0.5 M, ATP 50 mM, Glycerol 14.4%, Imidazole 1 M). The purified protein was analyzed by 10%-12% SDS-PAGE.

Incorporation of Phi29 Connector into Liposome:

1,2-diphytanoyl-sn-glycero-3-phosphocholine (DPhPC) was obtained from Avanti Polar Lipids. The procedure of the preparation of the phi29 proteoliposome was an amended version of a previous protocol (Danilo, 1997, CRC Press LLC; Haque et al., 2013, Nat. Protoc., 8, 373-392). Briefly, chloroform containing 1 mg DPhPC was evaporated off using rotary evaporator, and then phi29 connector and liposome rehydration buffer (liposome buffer: 3 M KCl, 250 mM sucrose, 5 mM HEPES, pH 7.4) were added and vortexed. To get homogenous proteoliposomes, prepared phi29 proteoliposomes were filtered through a 0.4 µm polycarbonate membrane for 20-30 times using the extruder (Avanti Polar Lipids).

Insertion of Phi29 Proteoliposome into the Copolymer Membrane of MinION Flow Cell:

MinION, blank MinION flow cells without pre-inserted biological pores and flow cell buffer were obtained from Oxford Nanopore Technologies Ltd. The MinION was connected to the computer, and a blank flow cell without biological nanopore was inserted into the MinION. The MinKNOW software, developed and provided by Oxford Nanopore Technologies Ltd., was used for pore insertion and data collection as per instructions provided. In brief, 20 µl [connector concentration: 200-500 µg/ml] of prepared proteoliposome was mixed with 280 µl flow cell buffer (25 mM potassium phosphate, 150 mM potassium ferrocyanide, 150 mM potassium ferricyanide, pH 8) and loaded into the priming port. MinKNOW was used to apply a voltage profile to facilitate phi29 channel insertion and subsequently to evaluate the number of channels with inserted phi29 connector. All data was viewed by a custom program provided by Oxford Nanopore Technologies Ltd.

Peptide Translocation:

Peptides were synthesized and purified by GenScript.

Peptide at a suitable concentration (1 to 20 µg/ml) was mixed with flow cell buffer and loaded into flow cell via priming port. MinKNOW was used to observe peptide translocation under different applied potentials. After collecting data, 1-2 ml flow cell buffer was used to flush the flow cell, allowing it to be reused. MinKNOW was used to confirm that there was no peptide remaining inside the MinION flow cell before loading the second peptide into the flow cell.

Electrophysiology Assay:

The free-standing lipid bilayer membrane was formed on the Teflon partition membrane (pore size: 200 µm). A pair of Ag/AgCl electrodes were placed in the cis- and trans- chambers. Bilayer Clamp Amplifier BC-535 (Warner Instruments) was connected to the Axon DigiData 1440 A analog-digital converter (Molecular Devices). Data was recorded at 1 kHz bandwidth and sampling frequency 20 kHz. The Clampex 10 (Molecular Devices) and Clampfit 10 (Molecular Devices) were used to collect and view data.

Results and Discussion

Insertion of the Channel of Phi29 DNA Packaging Motor into the Copolymeric Membrane of Oxford Nanopore Min-ION Flow Cell:

Phi29 connectors have been well characterized in electrophysiology experiments in lipid membranes (Geng et al., 2010, Biomaterials, 32, 8234-8242; Virology, 500, 285-291). Because of the hydrophobic mismatch between the Ph29 connector and the hydrophobic core of the lipid membranes, it is not straight forward to insert phi29 connectors directly into any hydrophobic membrane. Therefore, insertion of phi29 connector into lipid membranes has been generally carried out by fusing lipid membranes with lipid vesicles containing phi29 connector. When both vesicles and membranes are made of the same material and the hydrophobic tails of the molecules are of the same length, it is easier for molecules to mix. However, properties of copolymeric membranes are very different to that of lipid membranes. Hydrophobic tails of copolymeric membranes are of different lengths to that of lipid membranes and different in their chemistries; they are generally in a more disordered and entangled orientation in the membrane. The less fluidic and more stable nature of the copolymer makes it difficult for highly ordered lipid vesicles to fuse with.

Figure 5A:
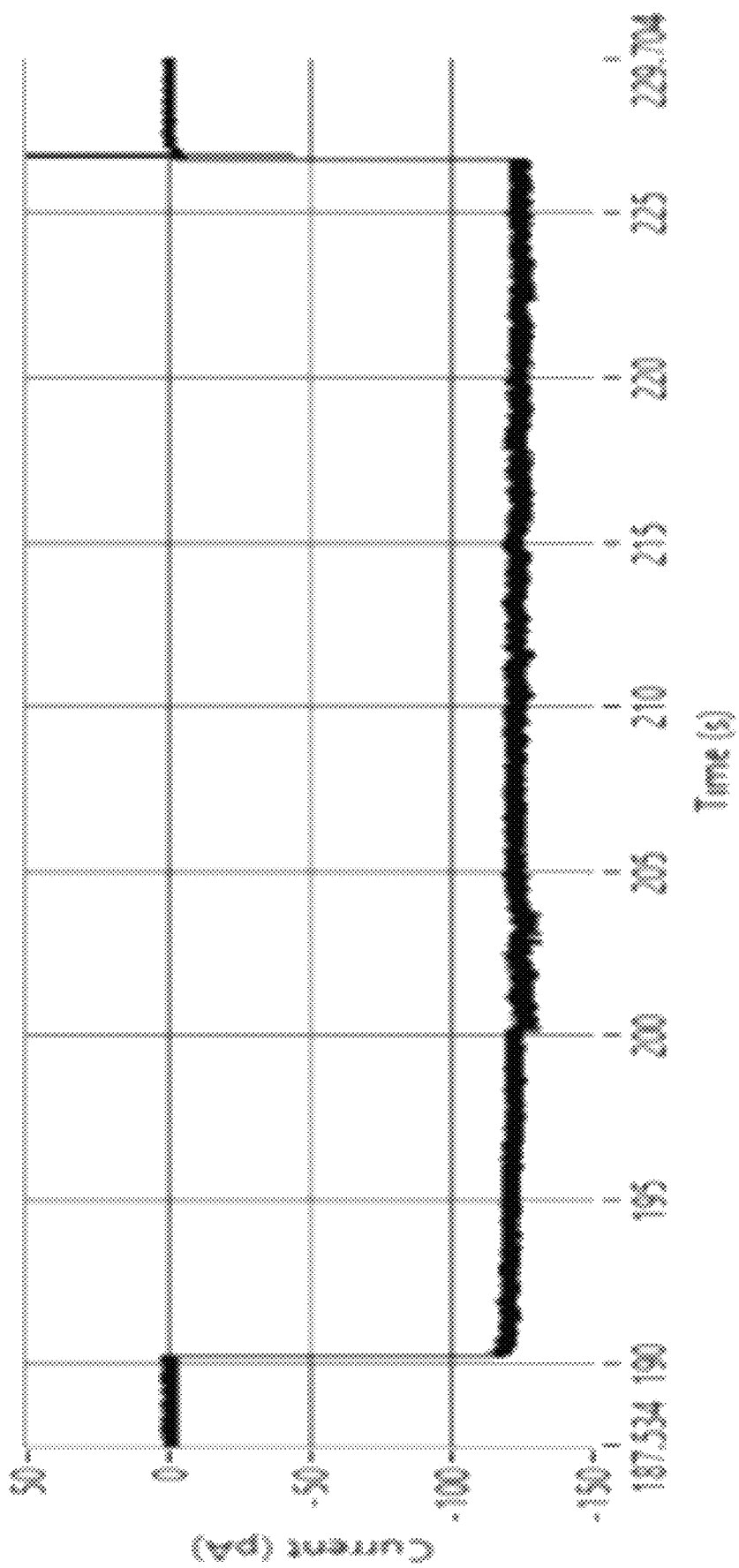
FIGS. 5A to 5C show the insertion of the channel of bacteriophage phi29 DNA packaging motor into the copolymer membrane of MinION flow cell.
Figure 5B:
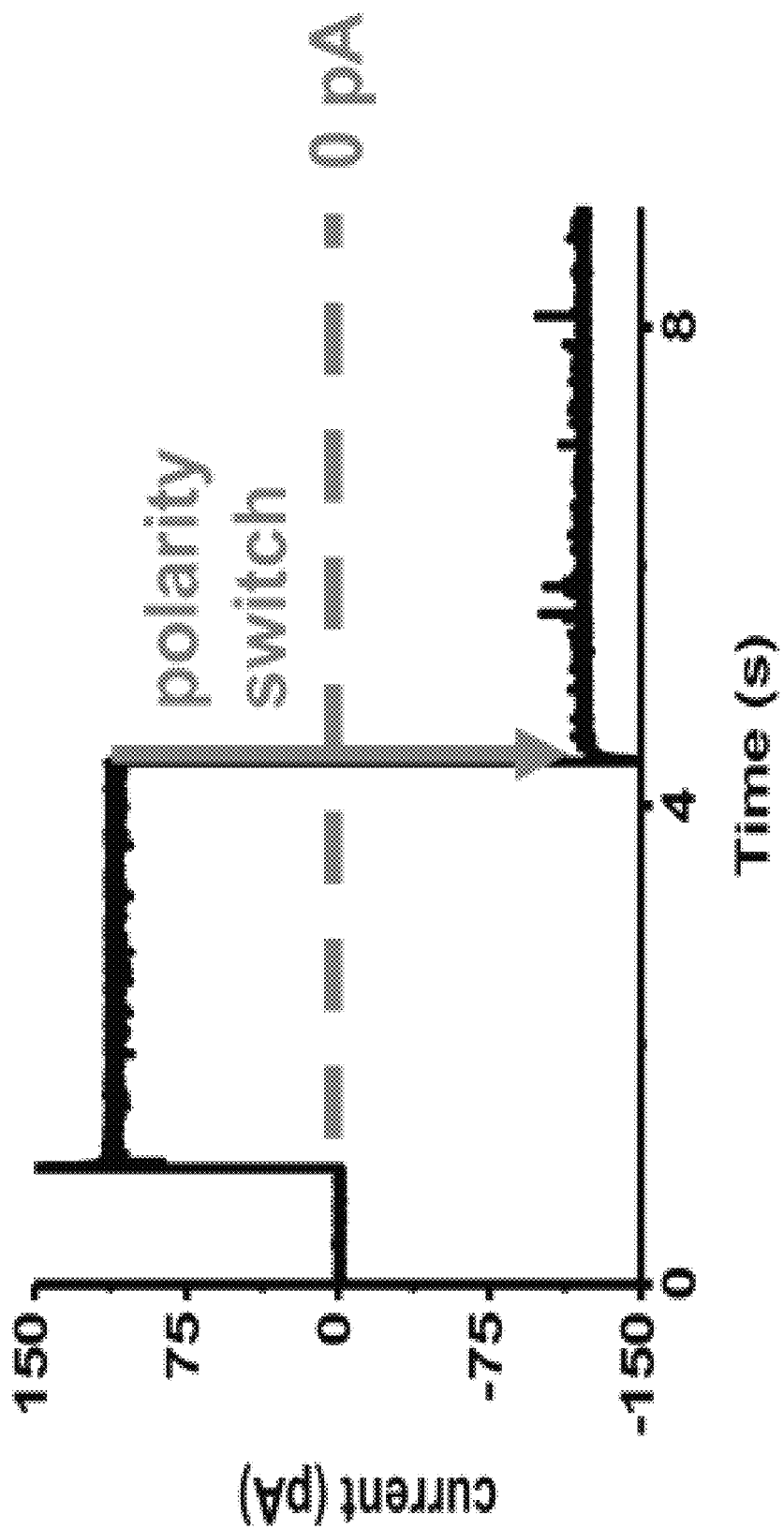

Surprisingly, results of this study have shown that phi29 connectors can be transferred from lipid vesicles into the copolymeric membranes of the MinION flow cell by fusing lipid vesicles with the copolymeric membrane. The phi29 channel insertion in the copolymeric membrane was also facilitated by an applied potential. Once the pore insertion was completed, inserted phi29 channels can be evaluated using MinKNOW by applying a voltage ranging from 50 mV to 500 mV. When 50 mV potential was applied, the current of a single phi29 channel inserted into the copolymeric membrane of the MinION flow cell was around 120 pA (FIG. 5a). In other words, in MinION flow cell buffer, a single phi29 channel inserted into the copolymeric membrane of the MinION flow cell had conductance of around 2.4 nS (Conductance=Current÷Voltage) (FIG. 5a). To confirm that 2.4 nS conductance channel represents a single phi29 channel inserted into copolymeric membrane of Min-ION flow cell, an electrophysiology experiment was carried out by inserting phi29 channels into lipid bilayer membrane via lipid vesicle fusion (FIG. 5b). When the electrophysiology experiment was carried out in MinION flow cell buffer provided by Oxford Nanopore Technologies Ltd., phi29 channels inserted into the lipid membrane also showed around 2.4 nS conductance confirming that the pores seen in MinION flow cell are indeed phi29 connector proteins. The insertion of multiple phi29 channels into a single copolymer membrane of MinION flow cell was also observed (data not shown).

Figure 5C:
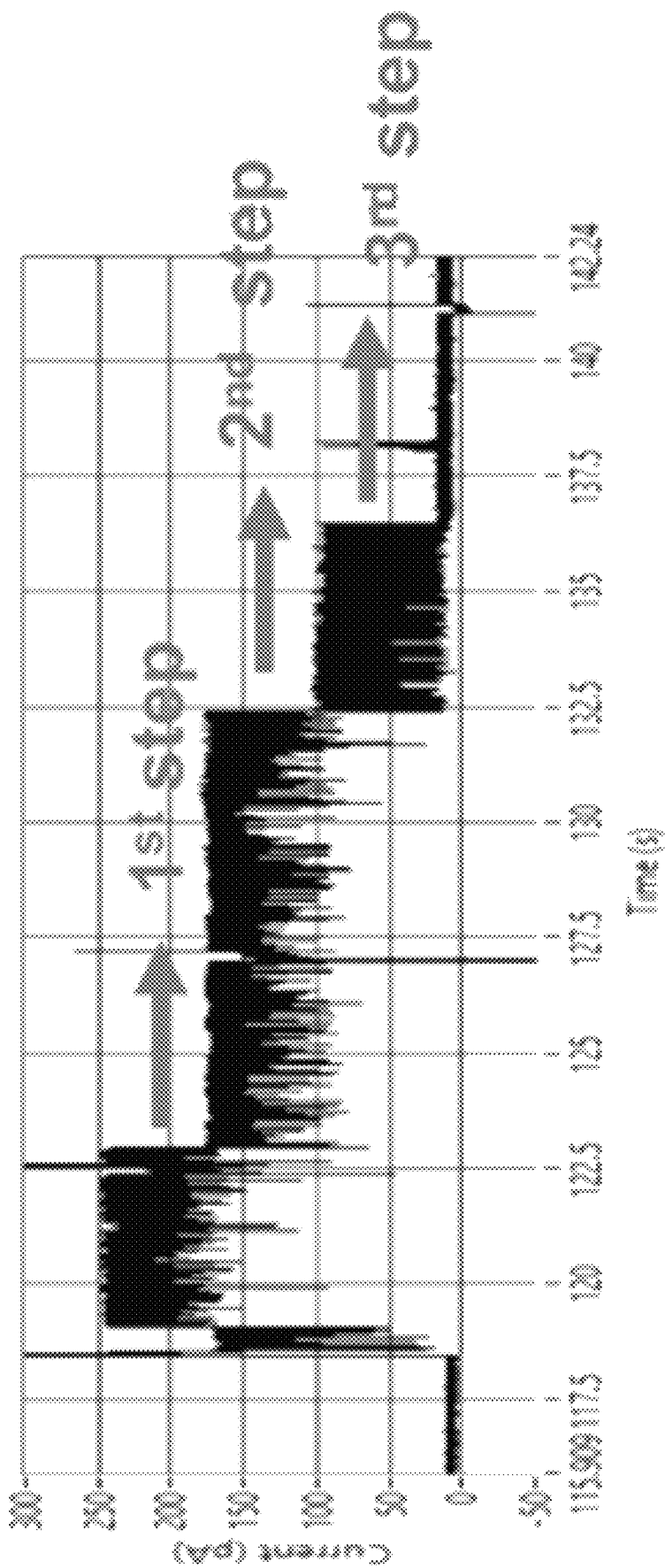

It has been shown that phi29 DNA packaging motor shows a characteristic three-step gating behavior when higher voltage (>100 mV) is applied (Geng et al., 2010, Biomaterials, 32, 8234-8242; Virology, 500, 285-291). Each step of gating represents a reduction in channel size by ~30%. To further confirm that the generated currents in MinION flow cells were owing to phi29 channel insertion, the voltage −100 mV was applied during platform QC process. The characteristic three-step gating behavior was observed under −100 mV, suggesting that the ~2.4 nS (240 pA±100 mV=2.4 nS) conductive channel in copolymeric membrane of the MinION flow cell represents a single phi29 channel (FIG. 5c).

Figure 6A:
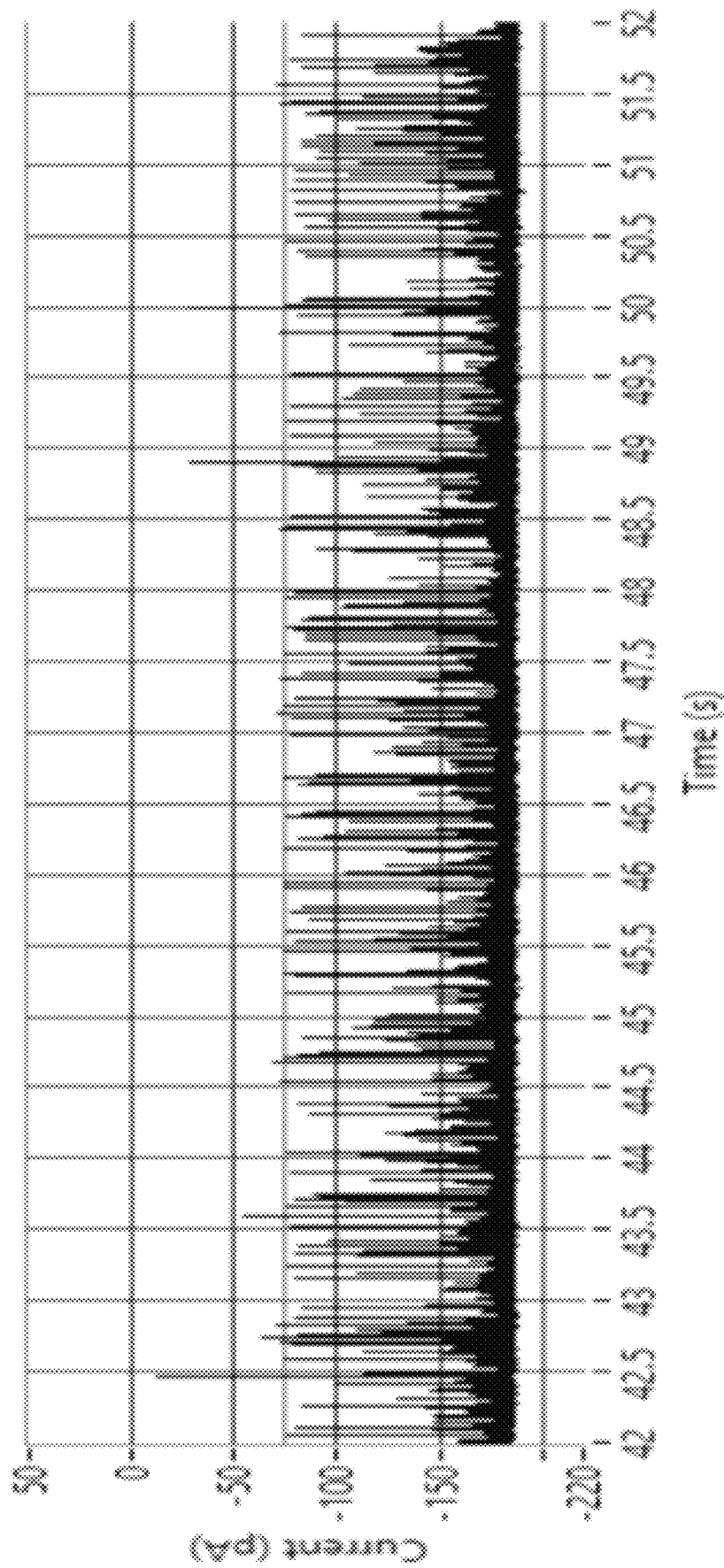
FIGS. 6A and 6B show the translocation of TAT peptides through the inserted phi29 channel of MinION flow cell under 75 mV (FIG. 6A) and 100 mV (FIG. 6B). Line indicates applied voltage.
Figure 6B:
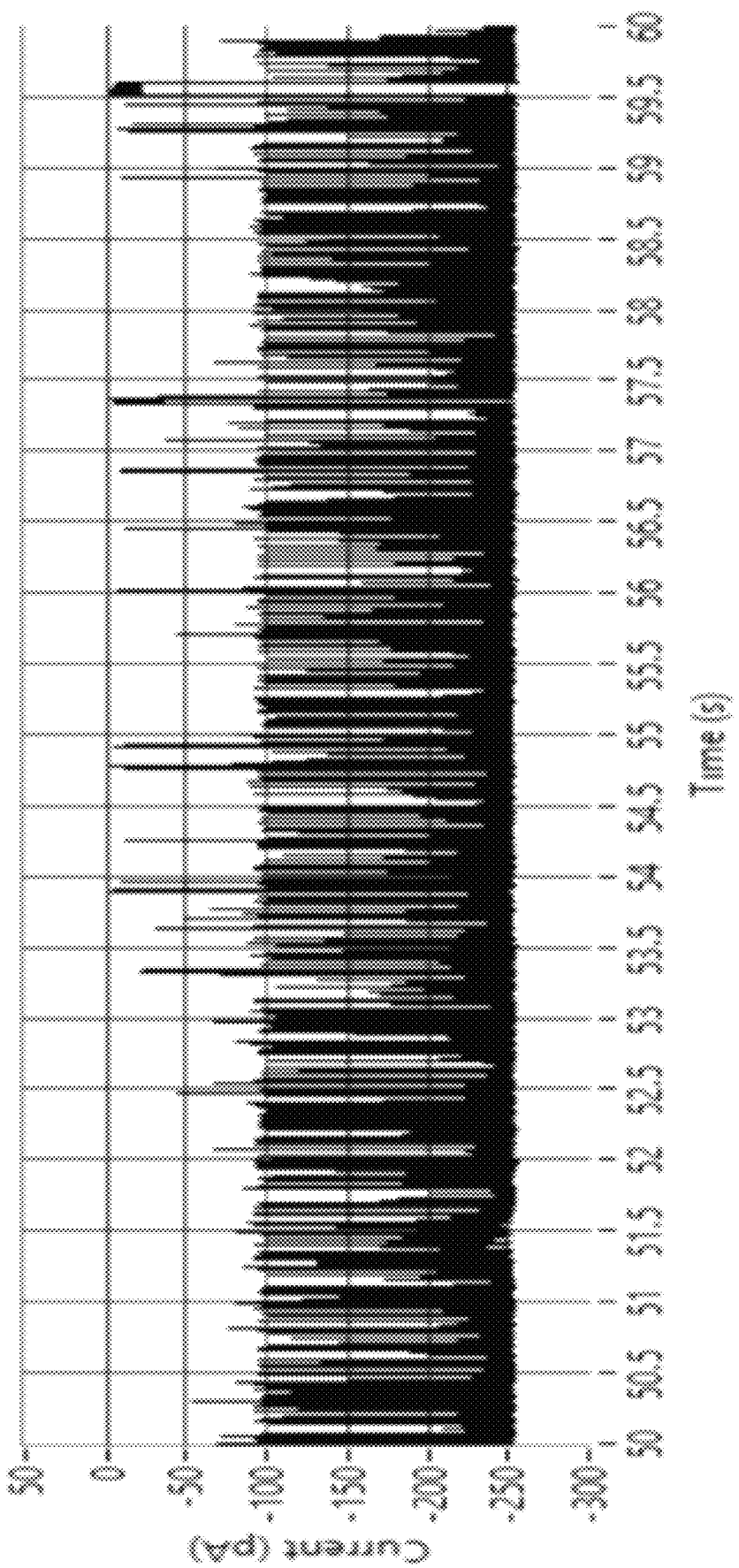
Figure 7A:
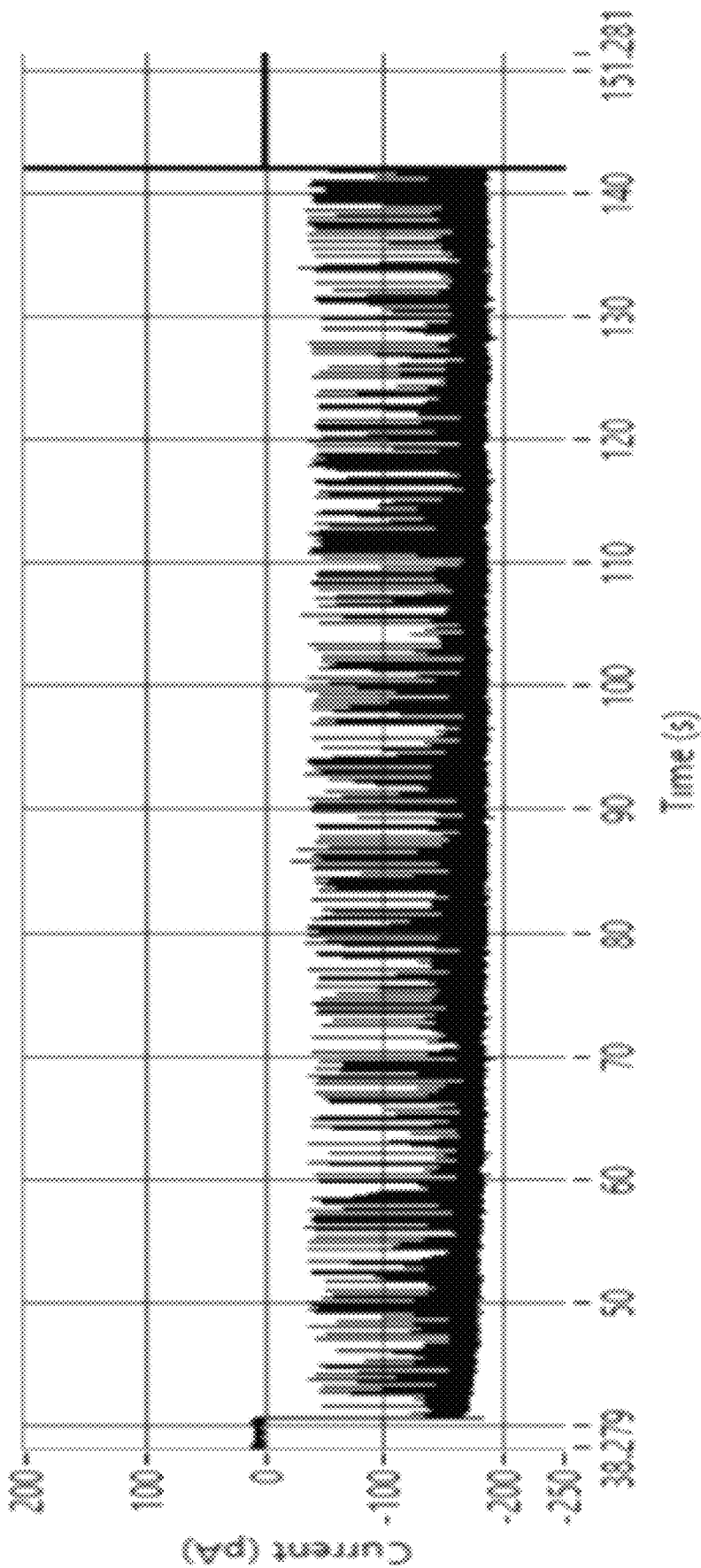
FIGS. 7A to 7D show the discrimination of different peptides by phi29 channel inserted in the MinION flow cell under 100 mV for TAT Peptide (FIG. 7A), R14 peptide (FIG. 7B), MAR peptide (FIG. 7C) and P27 peptide (FIG. 7D). Line indicates applied voltage.
Figure 7B:
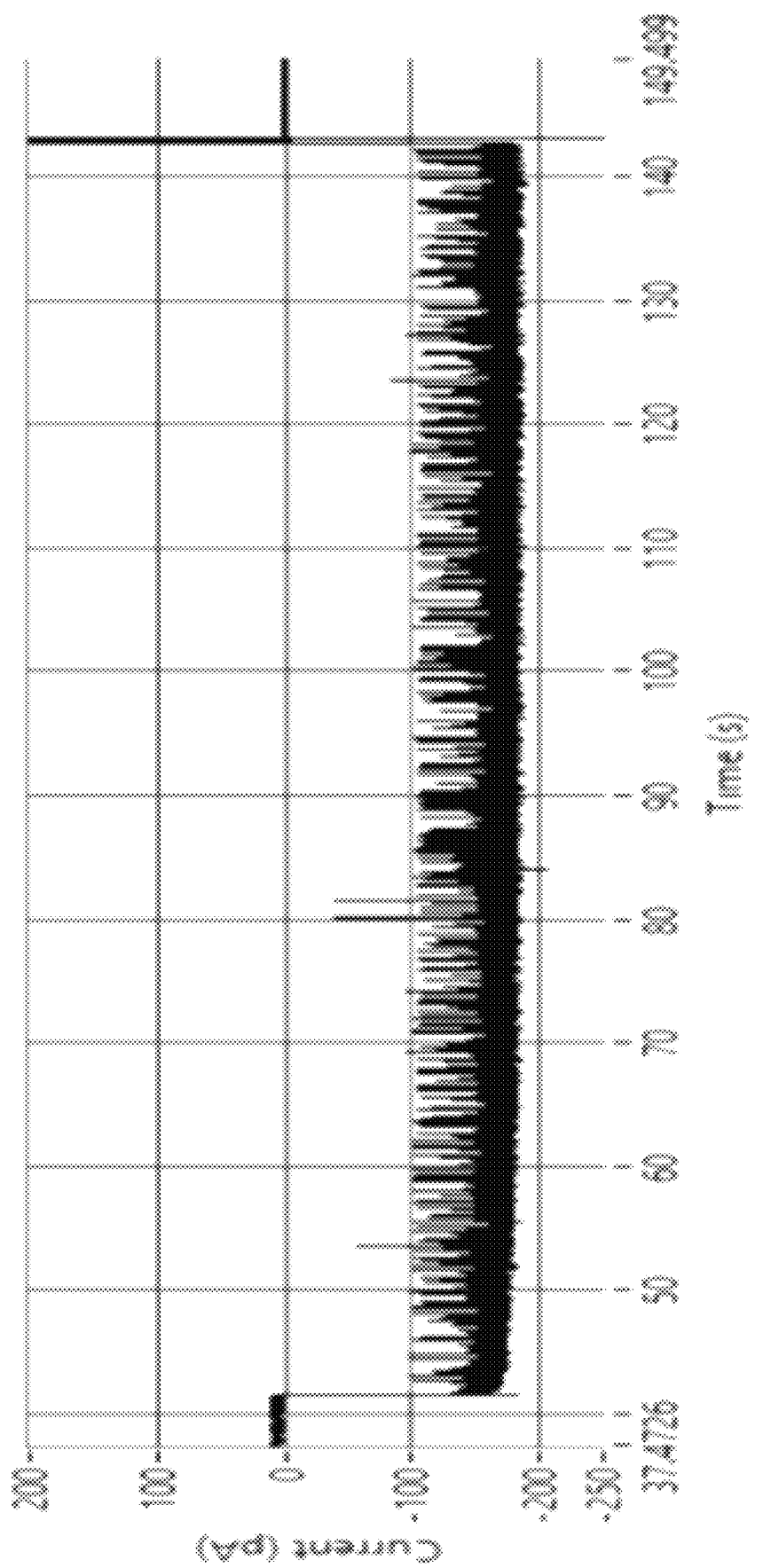
Figure 7C:
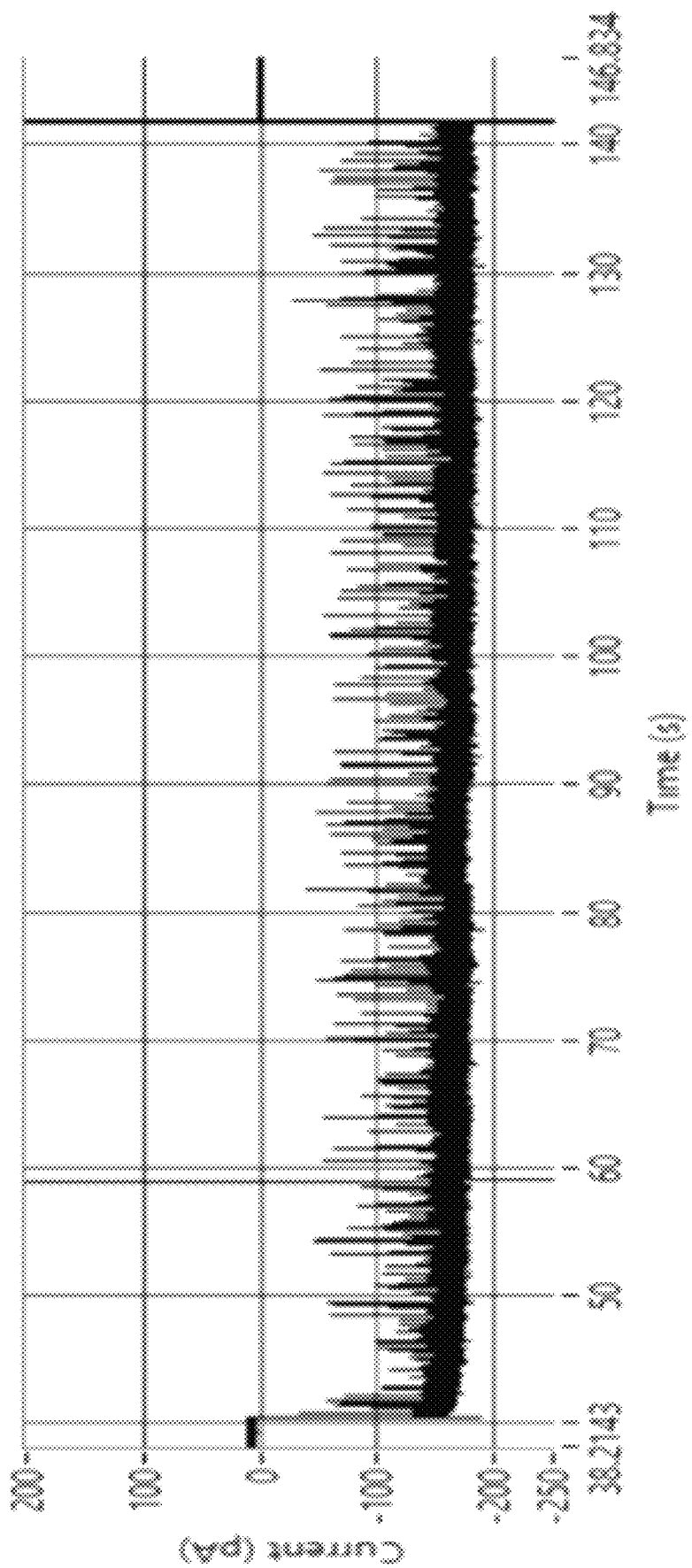
Figure 7D:
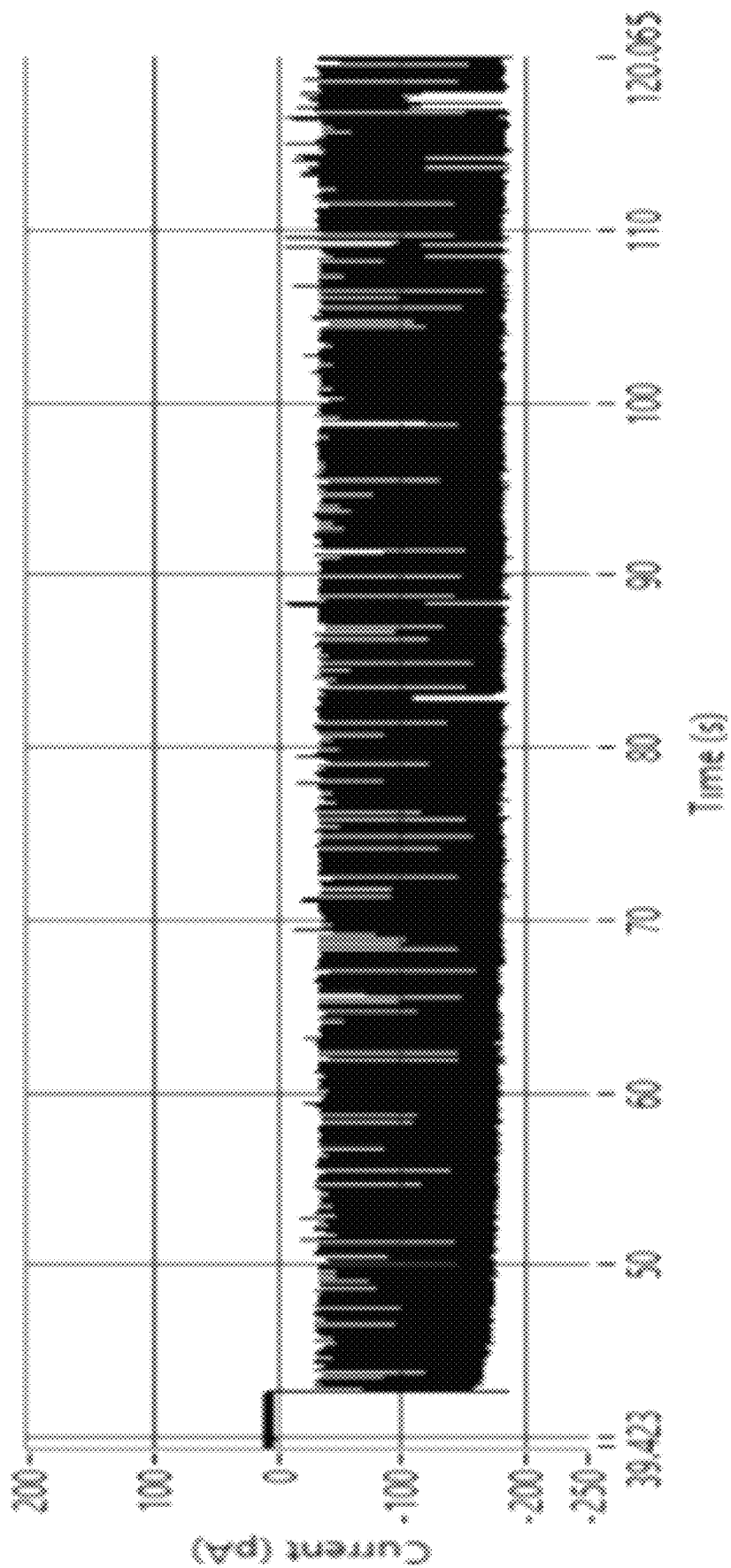

Differentiation of Four Peptides Using the Phi29 Motor Channel Inserted in the Copolymer Membrane of Oxford Nanopore MinION Flow Cell:

Success of phi29 insertion into copolymeric membranes of the MinION provides for high throughput analysis of phi29 channels. To explore potential biomedical applications of phi29 channel in MinION, four different peptides with different lengths and charge distribution were analyzed. Firstly, translocation of 12 amino acid long TAT peptide through the phi29 channel was analyzed under different voltages: 75 mV and 100 mV (FIG. 6). TAT peptide clearly translocated through the channel under both applied potentials. Within the same time duration, applying a higher voltage resulted in more TAT translocation events, indicating that the sensing of peptides through phi29 channel can be controlled with voltage. Secondly, all four peptides were translocated and detected one after the other through the same phi29 channel inserted into the copolymer of MinION flow cell (FIG. 7). Flow cell was washed with buffer after each peptide was translocated and before adding the next peptide. Each individual peptide can be discriminated using amplitude and the dwell time: TAT (FIG. 7a), MAR (FIG. 7b), R14 (FIG. 7c) and P27 (FIG. 7d). This experiment highlights the potential for the high-throughput capability of discriminating different peptides using a single flow cell in biomedical applications.

CONCLUSIONS

The channel of the DNA packaging motor of bacteriophage phi29 was inserted into the copolymer membrane of MinION flow cell by liposome-polymer fusion. The insertion was verified by the observation of three-step gating of phi29 channel. Different peptides were discriminated using inserted phi29 channels, showing the potential for high-throughput peptide sensing.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A copolymeric membrane comprising a nanopore inserted therein, wherein the nanopore is derived from a connector protein of a bacteriophage DNA packaging motor, wherein the nanopore comprises the aperture forming region of a connector protein of a bacteriophage DNA packaging motor, and wherein the aperture forming region is modified to alter one or more property of the channel of the nanopore.

2. The copolymeric membrane of claim 1, wherein the connector protein of a bacteriophage DNA packaging motor is modified compared to the wild-type connector protein.

3. The copolymeric membrane of claim 1, wherein the nanopore comprises a full length connector protein of a bacteriophage DNA packaging motor.

4. The copolymeric membrane of claim 1, wherein the nanopore comprises a truncated connector protein of a bacteriophage DNA packaging motor.

5. The copolymeric membrane of claim 1, wherein the nanopore is a multimeric protein formed of six or more subunits.

6. The copolymeric membrane of claim 5, wherein the nanopore is a dodecameric protein.

7. The copolymeric membrane of claim 5, wherein one or more of the subunits are modified at the C-terminus and/or N-terminus.

8. The copolymeric membrane of claim 7, wherein one or more of the subunits are modified at the C-terminus and/or N-terminus to increase the hydrophilicity at one or both ends of the nanopore.

9. The copolymeric membrane of claim 7, wherein one or more of the subunits are modified by the addition of a flexible linker and a peptide tag at the C-terminus and/or N-terminus.

10. The copolymeric membrane of claim 5, wherein the subunits are identical.

11. The copolymeric membrane of claim 1, wherein the bacteriophage DNA packaging motor is selected from the group consisting of phi29, T3, T4, T5, T7, SPP1, HK97, Lamda, G20c, P2, P3 and P22.

12. The copolymeric membrane of claim 1, wherein the copolymeric membrane is a triblock or diblock copolymeric membrane.

13. An array of copolymeric membranes according to claim 1.

14. The array of claim 13, which is adapted for insertion into a device suitable for detecting the translocation of analytes through the nanopores in the array.

15. A device comprising an array of copolymeric membranes according to claim 1.

16. A method of characterizing a target analyte, the method comprising applying a voltage potential across the copolymeric membrane of claim 1, contacting the copolymeric membrane with the target analyte such that the target analyte moves with respect to the nanopore, and taking one or more measurements as the target analyte moves with respect to the pore, thereby determining the presence, absence or one or more characteristics of the analyte.

* * * * *